(12) United States Patent
Brodsky et al.

(10) Patent No.: US 12,268,755 B2
(45) Date of Patent: Apr. 8, 2025

(54) ALLELE-SPECIFIC INACTIVATION OF MUTANT HTT VIA GENE EDITING AT CODING REGION SINGLE NUCLEOTIDE POLYMORPHISMS

(71) Applicant: University of Massachusetts, Boston, MA (US)

(72) Inventors: Michael Harry Brodsky, Sudbury, MA (US); Neil Aronin, Newtonville, MA (US); Sarah Rinde Oikemus, Holden, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 450 days.

(21) Appl. No.: 17/574,163

(22) Filed: Jan. 12, 2022

(65) Prior Publication Data
US 2022/0265852 A1 Aug. 25, 2022

Related U.S. Application Data

(60) Provisional application No. 63/136,378, filed on Jan. 12, 2021.

(51) Int. Cl.
*A61K 48/00* (2006.01)
*A61P 25/00* (2006.01)
*C12N 15/86* (2006.01)

(52) U.S. Cl.
CPC ........ *A61K 48/005* (2013.01); *A61K 48/0083* (2013.01); *A61K 48/0091* (2013.01); *A61P 25/00* (2018.01); *C12N 15/86* (2013.01)

(58) Field of Classification Search
None
See application file for complete search history.

(56) References Cited

U.S. PATENT DOCUMENTS

| | | | | |
|---|---|---|---|---|
| 2007/0259827 A1* | 11/2007 | Aronin | ........... | C12Y 115/01001 536/24.5 |
| 2017/0224843 A1* | 8/2017 | Deglon | ................ | A61K 38/465 |
| 2019/0055552 A1* | 2/2019 | Davidson | ............. | A61K 48/005 |

OTHER PUBLICATIONS

Uddin et al., "CRISPR Gene Therapy: Applications, Limitations, and Implications for the Future", Frontiers in Oncology, vol. 10, Published Aug. 7, 2020, pp. 1-14. (Year: 2020).*
Ekman et al., "CRISPR-Cas9-Mediated Genome Editing Increases Lifespan and Improves Motor Deficits in a Huntington's Disease Mouse Model", Molecular Therapy Nucleic Acids, vol. 17, Published Sep. 2019, pp. 829-836. (Year: 2019).*
Lessard et al., "Human genetic variation alters CRISPR-Cas9 on-and off-targeting specificity at therapeutically implicated loci", PNAS, Published Dec. 11, 2017, pp. E11257-E11266. (Year: 2017).*
Alterman, J. F. et al. (2019) "A divalent siRNA chemical scaffold for potent and sustained modulation of gene expression throughout the central nervous system," *Nature Biotechnology* 37(8), 884-894.
Altschul, S. F. et al. (1990) "Basic local alignment search tool," *Journal of Molecular Biology* 215(3), 403-410.
Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.
Burrus, C. J. et al. (2020) "Striatal Projection Neurons Require Huntingtin for Synaptic Connectivity and Survival," *Cell Reports* 30(3), 642-657.e646.
Chao, M. J. et al. (2017) "Haplotype-based stratification of Huntington's disease," *European Journal of Human Genetics* 25(11), 1202-1209.
Choudhury, S. R. et al. (2016) "Widespread Central Nervous System Gene Transfer and Silencing After Systemic Delivery of Novel AAV-AS Vector," *Molecular Therapy* 24(4), 726-735.
Didiot, M.-C. et al. (2018) "Nuclear Localization of Huntingtin mRNA Is Specific to Cells of Neuronal Origin," *Cell Reports* 24(10), 2553-2560.e2555.
Dieffenbach, C. W. et al. (1995) *PCR Primer, A Laboratory Manual*, Cold Spring Harbor Laboratory Press, Plainview, N.Y.
Doudna, J. A. et al. (2014) "Genome editing. The new frontier of genome engineering with CRISPR-Cas9," *Science* 346(6213), Article No. 1258096.
Dragatsis, I. et al. (2000) "Inactivation of Hdh in the brain and testis results in progressive neurodegeneration and sterility in mice," *Nature Genetics* 26(3), 300-306.
Evers, M. M. et al. (2018) "AAV5-miHTT Gene Therapy Demonstrates Broad Distribution and Strong Human Mutant Huntingtin Lowering in a Huntington's Disease Minipig Model," *Molecular Therapy* 26(9), 2163-2177.
Fu, Y. et al. (2014) "Improving CRISPR-Cas nuclease specificity using truncated guide RNAs," *Nature Biotechnology* 32(3), 279-284.
Garriga-Canut, M. et al. (2012) "Synthetic zinc finger repressors reduce mutant huntingtin expression in the brain of R6/2 mice," *Proceedings of the National Academy of Sciences* 109(45), E3136.
Gray, M. et al. (2008) "Full-Length Human Mutant Huntingtin with a Stable Polyglutamine Repeat Can Elicit Progressive and Selective Neuropathogenesis in BACHD Mice," *Journal of Neuroscience* 28(24), 6182.

(Continued)

*Primary Examiner* — Brian Whiteman
*Assistant Examiner* — Stephanie L Sullivan
(74) *Attorney, Agent, or Firm* — Medlen & Carroll, LLP

(57) ABSTRACT

The present invention contemplates-allele-specific gene editing based on targeting a heterozygous single nucleotide polymorphism (SNP) in a protein coding sequence associated with a genetic disease. The data shown herein demonstrates that the outcome of such gene editing creates a nonesense mutation that results in a marked and selective reduction of mutant protein without affecting wild type protein expression. Expression of a single CRISPR-Cas9 nuclease in neurons generated a high frequency of mutations in the targeted HD allele that included both small insertion/deletion mutations and viral vector insertions. Thus, as disclosed herein, allele-specific targeting of InDel and insertion mutations to heterozygous coding SNPs provides a feasible approach to inactivate autosomal dominant mutations that cause genetic disease.

11 Claims, 17 Drawing Sheets

Specification includes a Sequence Listing.

(56) References Cited

OTHER PUBLICATIONS

Hanlon, K. S. et al. (2019) "High levels of AAV vector integration into CRISPR-induced DNA breaks," *Nature Communications* 10(1), 4439.
Harper, S. Q. et al. (2005) "RNA interference improves motor and neuropathological abnormalities in a Huntington's disease mouse model," *Proceedings of the National Academy of Sciences of the United States of America* 102(16), 5820.
Heidenreich, M. et al. (2016) "Applications of CRISPR-Cas systems in neuroscience," *Nature Reviews. Neuroscience* 17(1), 36-44.
Hindson, B. J. et al. (2011) "High-Throughput Droplet Digital PCR System for Absolute Quantitation of DNA Copy Number," *Analytical Chemistry* 83(22), 8604-8610.
Liu, J.-P. et al. (2017) "Is Huntingtin Dispensable in the Adult Brain?," *Journal of Huntington's disease* 6(1), 1-17.
McColgan, P. et al. (2018) "Huntington's disease: a clinical review," *European Journal of Neurology* 25(1), 24-34.
McKinstry, S. U. et al. (2014) "Huntingtin Is Required for Normal Excitatory Synapse Development in Cortical and Striatal Circuits," *Journal of Neuroscience* 34(28), 9455.
Mehler, M. F. et al. (2019) "Loss-of-Huntingtin in Medial and Lateral Ganglionic Lineages Differentially Disrupts Regional Interneuron and Projection Neuron Subtypes and Promotes Huntington's Disease-Associated Behavioral, Cellular, and Pathological Hallmarks," Journal of Neuroscience 39(10), 1892.
Merienne, N. et al. (2017) "The Self-Inactivating KamiCas9 System for the Editing of CNS Disease Genes," *Cell Reports* 20(12), 2980-2991.
Miniarikova, J. et al. (2017) "AAV5-miHTT gene therapy demonstrates suppression of mutant huntingtin aggregation and neuronal dysfunction in a rat model of Huntington's disease," *Gene Therapy* 24(10), 630-639.
Monteys, A. M. et al. (2017) "CRISPR/Cas9 Editing of the Mutant Huntingtin Allele In Vitro and In Vivo," *Molecular Therapy* 25(1), 12-23.
Pfister, E. L. et al. (2009) "Five siRNAs Targeting Three SNPs May Provide Therapy for Three-Quarters of Huntington's Disease Patients," *Current Biology* 19(9), 774-778.
Pinello, L. et al. (2016) "Analyzing CRISPR genome-editing experiments with CRISPResso," *Nature Biotechnology* 34(7), 695-697.
Popp, M. W.-L. et al. (2013) "Organizing Principles of Mammalian Nonsense-Mediated mRNA Decay," *Annual Review of Genetics* 47(1), 139-165.
Sah, D. W. Y. et al. (2011) "Oligonucleotide therapeutic approaches for Huntington disease," *Journal of clinical investigation* 121(2), 500-507.
Sena-Esteves, M. et al. (2004) "Optimized large-scale production of high titer lentivirus vector pseudotypes," *Journal of Virological Methods* 122(2), 131-139.
Shin, J. W. et al. (2016) "Permanent inactivation of Huntington's disease mutation by personalized allele-specific CRISPR/Cas9," *Human Molecular Genetics* 25(20), 4566-4576.
Snell, R. G. et al. (1993) "Relationship between trinucleotide repeat expansion and phenotypic variation in Huntington's disease," *Nature Genetics* 4(4), 393-397.
Vachey, G. et al. (2018) "CRISPR/Cas9-Mediated Genome Editing for Huntington's Disease," *Methods in Molecular Biology* 1780, 463-481.
Walter, D. M. et al. (2017) "Systematic In Vivo Inactivation of Chromatin-Regulating Enzymes Identifies Setd2 as a Potent Tumor Suppressor in Lung Adenocarcinoma," *Cancer Research* 77(7), 1719-1729.
Wang, G. et al. (2016) "Ablation of huntingtin in adult neurons is nondeleterious but its depletion in young mice causes acute pancreatitis," *Proceedings of the National Academy of Sciences* 113(12), 3359.
Zeitler, B. et al. (2019) "Allele-selective transcriptional repression of mutant HTT for the treatment of Huntington's disease," *Nature Medicine* 25(7), 1131-1142.

Zeitlin, S. et al. (1995) "Increased apoptosis and early embryonic lethality in mice nullizygous for the Huntington's disease gene homologue," *Nature Genetics* 11(2), 155-163.
Alterman, J. F. et al., (2019) "A divalent siRNA chemical scaffold for potent and sustained modulation of gene expression throughout the central nervous system," *Nat. Biotechnol.* 37(8), 884-894.
Altschul, S. F. et al., (1990) "Basic local alignment search tool," *J. Mol. Biol.* 215(3), 403-410.
Anderson, M. L. M. and Young, B. D., (1985) "Quantitative Filter Hybridization," in *Nucleic Acid Hybridisation: A Practical Approach* (Hames, B. D. and Higgins, S. J., Eds.), pp. 73-111, Oxford University Press, USA.
Aronin, N. et al., (1995) "CAG expansion affects the expression of mutant Huntingtin in the Huntington's disease brain," *Neuron* 15(5), 1193-1201.
Burrus, C. J. et al., (2020) "Striatal Projection Neurons Require Huntingtin for Synaptic Connectivity and Survival," *Cell Rep.* 30(3), 642-657.e646.
Chao, M. J. et al., (2017) "Haplotype-based stratification of Huntington's disease," *Eur. J. Hum. Genet.* 25(11), 1202-1209.
Choudhury, S. R. et al., (2016) "Widespread Central Nervous System Gene Transfer and Silencing After Systemic Delivery of Novel AAV-AS Vector," *Mol. Ther.* 24(4), 726-735.
Cong, L. et al., (2013) "Multiplex Genome Engineering Using CRISPR/Cas Systems," *Science (New York, N.Y.)* 339(6121), 819-823.
Didiot, M.-C. et al., (2018) "Nuclear Localization of Huntingtin mRNA Is Specific to Cells of Neuronal Origin," *Cell Rep.* 24(10), 2553-2560.e2555.
Dieffenbach, C. W. and Dveksler, G. S., (1995) *PCR Primer, A Laboratory Manual,* Cold Spring Harbor Laboratory Press, Plainview, N.Y.
DiFiglia, M. et al., (1995) "Huntingtin is a cytoplasmic protein associated with vesicles in human and rat brain neurons," *Neuron* 14(5), 1075-1081.
Doudna, J. A. and Charpentier, E., (2014) "Genome editing. The new frontier of genome engineering with CRISPR-Cas9," *Science* 346(6213), Article No. 1258096.
Dragatsis, I. et al., (2000) "Inactivation of Hdh in the brain and testis results in progressive neurodegeneration and sterility in mice," *Nat. Genet.* 26(3), 300-306.
Evers, M. M. et al., (2018) "AAV5-miHTT Gene Therapy Demonstrates Broad Distribution and Strong Human Mutant Huntingtin Lowering in a Huntington's Disease Minipig Model," *Mol. Ther.* 26(9), 2163-2177.
Fu, Y. et al., (2014) "Improving CRISPR-Cas nuclease specificity using truncated guide RNAs," *Nat. Biotechnol.* 32(3), 279-284.
Garriga-Canut, M. et al., (2012) "Synthetic zinc finger repressors reduce mutant huntingtin expression in the brain of R6/2 mice," *P.N.A.S.* 109(45), E3136.
Gray, M. et al., (2008) "Full-Length Human Mutant Huntingtin with a Stable Polyglutamine Repeat Can Elicit Progressive and Selective Neuropathogenesis in BACHD Mice," *J. Neurosci.* 28(24), 6182.
Hanlon, K. S. et al., (2019) "High levels of AAV vector integration into CRISPR-induced DNA breaks," *Nat. Commun.* 10(1), 4439.
Harper, S. Q. et al., (2005) "RNA interference improves motor and neuropathological abnormalities in a Huntington's disease mouse model," *Proc. Natl. Acad. Sci. U. S. A.* 102(16), 5820.
Hatch, A. C. et al., (2011) "1-Million droplet array with wide-field fluorescence imaging for digital PCR," *Lab on a Chip* 11(22), 3838-3845.
Heidenreich, M. and Zhang, F., (2016) "Applications of CRISPR-Cas systems in neuroscience," *Nat. Rev. Neurosci.* 17(1), 36-44.
Hindson, B. J. et al., (2011) "High-Throughput Droplet Digital PCR System for Absolute Quantitation of DNA Copy Number," *Anal. Chem.* 83(22), 8604-8610.
Hodgson, J. G. et al., (1999) "A YAC Mouse Model for Huntington's Disease with Full- Length Mutant Huntingtin, Cytoplasmic Toxicity, and Selective Striatal Neurodegeneration," *Neuron* 23(1), 181-192.
Hsu, P. D. et al., (2014) "Development and applications of CRISPR-Cas9 for genome engineering," *Cell* 157(6), 1262-1278.

(56) References Cited

OTHER PUBLICATIONS

Huntingtons Disease Collaborative et al., (1993) "A novel gene containing a trinucleotide repeat that is expanded and unstable on Huntington's disease chromosomes," Cell 72(6), 971-983.
Jinek, M. et al., (2012) "A programmable dual-RNA-guided DNA endonuclease in adaptive bacterial immunity," Science 337(6096), 816-821.
Keeler, A. M. et al., (2016) "Cellular Analysis of Silencing the Huntington's Disease Gene Using AAV9 Mediated Delivery of Artificial Micro RNA into the Striatum of Q140/Q140 Mice," Journal of Huntington's Disease 5(3), 239-248.
Kordasiewicz, Holly B. et al., (2012) "Sustained Therapeutic Reversal of Huntington's Disease by Transient Repression of Huntingtin Synthesis," Neuron 74(6), 1031-1044.
Liu, J.-P. and Zeitlin, S. O., (2017) "Is Huntingtin Dispensable in the Adult Brain?," Journal of Huntington's disease 6(1), 1-17.
McColgan, P. and Tabrizi, S. J., (2018) "Huntington's disease: a clinical review," Eur. J. Neurol. 25(1), 24-34.
McCullough, K. T. et al., (2019) "Somatic Gene Editing of GUCY2D by AAV-CRISPR/Cas9 Alters Retinal Structure and Function in Mouse and Macaque," Human Gene Therapy 30(5), 571-589.
McKinstry, S. U. et al., (2014) "Huntingtin Is Required for Normal Excitatory Synapse Development in Cortical and Striatal Circuits," J. Neurosci. 34(28), 9455.
Mehler, M. F. et al., (2019) "Loss-of-Huntingtin in Medial and Lateral Ganglionic Lineages Differentially Disrupts Regional Interneuron and Projection Neuron Subtypes and Promotes Huntington's Disease-Associated Behavioral, Cellular, and Pathological Hallmarks," J. Neurosci. 39(10), 1892.
Merienne, N. et al., (2017) "The Self-Inactivating KamiCas9 System for the Editing of CNS Disease Genes," Cell Rep. 20(12), 2980-2991.
Miniarikova, J. et al., (2017) "AAV5-miHTT gene therapy demonstrates suppression of mutant huntingtin aggregation and neuronal dysfunction in a rat model of Huntington's disease," Gene Ther. 24(10), 630-639.
Monteys, A. M. et al., (2017) "CRISPR/Cas9 Editing of the Mutant Huntingtin Allele In Vitro and In Vivo," Mol. Ther. 25(1), 12-23.
Palacios, I. M., (2013) "Nonsense-mediated mRNA decay: from mechanistic insights to impacts on human health," Briefings in Functional Genomics 12(1), 25-36.
Pfister, E. L. et al., (2018) "Artificial miRNAs Reduce Human Mutant Huntingtin Throughout the Striatum in a Transgenic Sheep Model of Huntington's Disease," Human gene therapy 29(6), 663-673.
Pfister, E. L. et al., (2009) "Five siRNAs Targeting Three SNPs May Provide Therapy for Three-Quarters of Huntington's Disease Patients," Curr. Biol. 19(9), 774-778.
Pinello, L. et al., (2016) "Analyzing CRISPR genome-editing experiments with CRISPResso," Nat. Biotechnol. 34(7), 695-697.
Platt, R. J. et al., (2014) "CRISPR-Cas9 knockin mice for genome editing and cancer modeling," Cell 159(2), 440-455.
Popp, M. W.-L. and Maquat, L. E., (2013) "Organizing Principles of Mammalian Nonsense-Mediated mRNA Decay," Annu. Rev. Genet. 47(1), 139-165.
Sah, D. W. Y. and Aronin, N., (2011) "Oligonucleotide therapeutic approaches for Huntington disease," Journal of clinical investigation 121(2), 500-507.
Sena-Esteves, M. et al., (2004) "Optimized large-scale production of high titer lentivirus vector pseudotypes," J. Virol. Methods 122(2), 131-139.
Shin, J. W. et al., (2016) "Permanent inactivation of Huntington's disease mutation by Personalized allele-specific CRISPR/Cas9," Hum. Mol. Genet. 25(20), 4566-4576.
Snell, R. G. et al., (1993) "Relationship between trinucleotide repeat expansion and phenotypic variation in Huntington's disease," Nat. Genet. 4(4), 393-397.
Stanek, L. M. et al., (2014) "Silencing mutant huntingtin by adeno-associated virus-mediated RNA interference ameliorates disease manifestations in the YAC128 mouse model of Huntington's disease," Human gene therapy 25(5), 461-474.
Vachey, G. and Déglon, N., (2018) "CRISPR/Cas9-Mediated Genome Editing for Huntington's Disease," Methods Mol. Biol. 1780, 463-481.
Veitch, N. J. et al., (2007) "Inherited CAG•CTG allele length is a major modifier of somatic mutation length variability in Huntington disease," DNA Repair 6(6), 789-796.
Walter, D. M. et al., (2017) "Systematic In Vivo Inactivation of Chromatin-Regulating Enzymes Identifies Setd2 as a Potent Tumor Suppressor in Lung Adenocarcinoma," Cancer Res. 77(7), 1719-1729.
Wang, G. et al., (2016) "Ablation of huntingtin in adult neurons is nondeleterious but its depletion in young mice causes acute pancreatitis," P.N.A.S. 113(12), 3359.
Wilson, K. A. et al., (2013) "Design and Development of Artificial Zinc Finger Transcription Factors and Zinc Finger Nucleases to the hTERT Locus," Molecular Therapy—Nucleic Acids 2(4), Article No. e87.
Yang, S. et al., (2017) "CRISPR/Cas9-mediated gene editing ameliorates neurotoxicity in mouse model of Huntington's disease," Journal of Clinical Investigation 127(7), 2719-2724.
Zeitler, B. et al., (2019) "Allele-selective transcriptional repression of mutant HTT for the treatment of Huntington's disease," Nat. Med. 25(7), 1131-1142.
Zeitlin, S. et al., (1995) "Increased apoptosis and early embryonic lethality in mice nullizygous for the Huntington's disease gene homologue," Nat. Genet. 11(2), 155-163.
Zhu, L. J. et al., (2014) "CRISPRseek: A Bioconductor Package to Identify Target-Specific Guide RNAs for CRISPR-Cas9 Genome-Editing Systems," PLoS One 9(9), Article No. e108424.

* cited by examiner

FIG. 1B  Non-target allele  ex50C  CCTCATCACTGTGTGCACTTCA  SEQ ID NO: 14
         Htt Target allele  ex50T  CCTCATCACTGTGTGCACTTCA  SEQ ID NO: 15

FIG. 10A 4 week post-injection, side 1
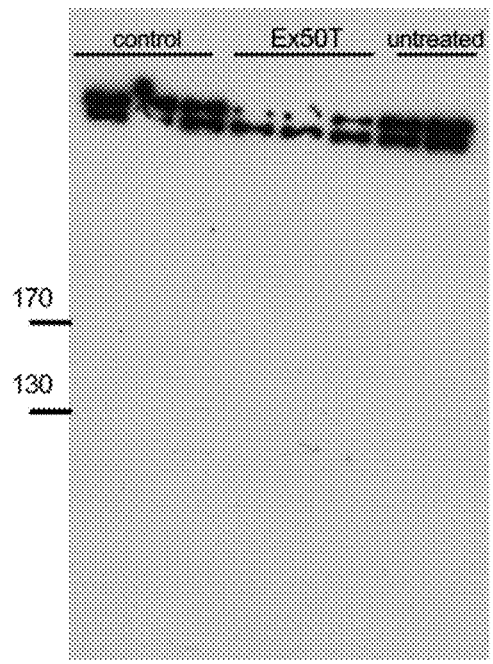
FIG. 10B week post-injection, side 2
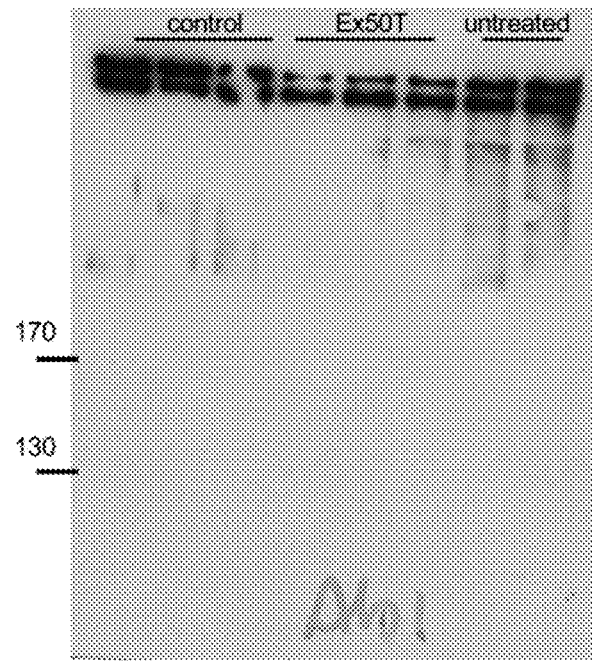
FIG. 10C 6 week post-injection, side 1
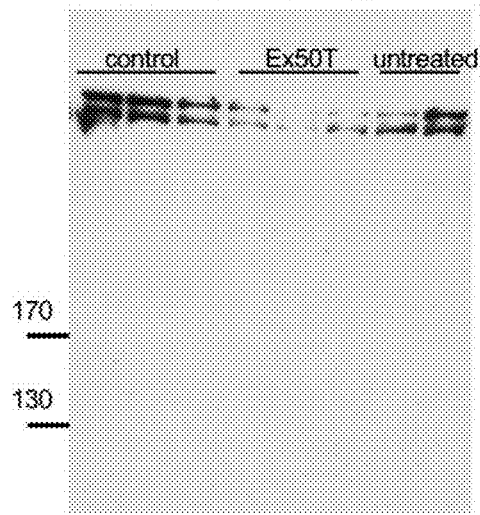
FIG. 10D 6 week post-injection, side 2
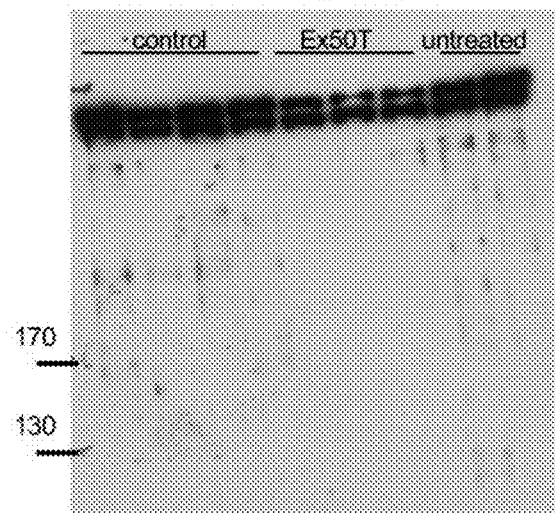

Injected side Anti-RFP
  Injected side Anti-IBA-1
  uninjected
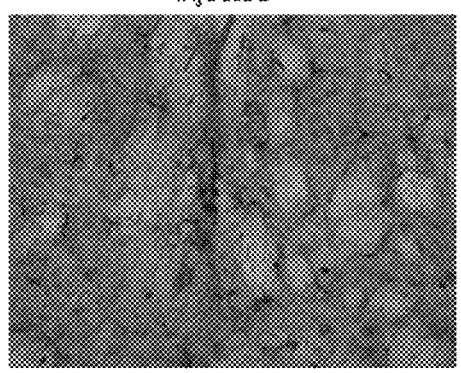 injected Anti-IBA-1

| | cleavage | SNP | | |
|---|---|---|---|---|
| control | ▼ | ▼ | | |
| C G A G C T G C C T : G C A G A A C C G G | | | 49.45% (3168 reads) | SEQ ID NO: 64 |
| C G A G C T G C C T : G C A G A G C C G G | | | 46.64% (2975 reads) | SEQ ID NO: 65 |

Ex48Gg2 treated

| | | | |
|---|---|---|---|
| C G A G C T G C C T : G C A G A A C C G G | 51.58% (2621 reads) | SEQ ID NO: 66 |
| C G A G C T G C C T : G C A G A G C C G G | 32.51% (1652 reads) | SEQ ID NO: 67 |
| G A G C T G C C [T] T : G C A G A G C C G G | 4.47% (227 reads) | SEQ ID NO: 68 |
| C G A G - - - - C T : G C A G A G C C G G | 1.34% (68 reads) | SEQ ID NO: 69 |
| C G C G C T G C C T : G C A G A A C C G G | 1.34% (68 reads) | SEQ ID NO: 70 |
| C G A G C T G C C T : G C C G A A C C G G | 0.77% (39 reads) | SEQ ID NO: 71 |
| C G A G C T - - T : G C A G A G C C G G | 0.77% (39 reads) | SEQ ID NO: 72 |
| C G C G C T G C C T : G C A G A G C C G G | 0.65% (33 reads) | SEQ ID NO: 73 |
| C G A - - - G C C T : G C A G A G C C G G | 0.61% (31 reads) | SEQ ID NO: 74 |
| C G A G C T G C C T : G C C G A G C C G G | 0.53% (27 reads) | SEQ ID NO: 75 |
| C G A G C T G C C T : - C A G A G C C G G | 0.33% (17 reads) | SEQ ID NO: 76 |
| C G A G - - - - T : G C A G A G C C G G | 0.31% (16 reads) | SEQ ID NO: 77 |
| C G A G C T G C C T : - - A G A G C C G G | 0.28% (14 reads) | SEQ ID NO: 78 |
| A G C T G C C [T G] T : G C A G A G C C G G | 0.20% (10 reads) | SEQ ID NO: 79 |
| C G A G C T G - C T : G C A G A G C C G G | 0.20% (10 reads) | SEQ ID NO: 80 |
| G A G C T G [T] G C T : G C A G A G C C G G | 0.20% (10 reads) | SEQ ID NO: 81 |
| C G A G C T G C C - : G C A G A G C C G G | 0.18% (9 reads) | SEQ ID NO: 82 |
| C G A G C T G - C G : G C A G A G C C G G | 0.18% (9 reads) | SEQ ID NO: 83 |
| A G C T G C C [T A] T : G C A G A G C C G G | 0.18% (8 reads) | SEQ ID NO: 84 |
| C G A G C T G C C T : G C A G A A C C G C | 0.14% (7 reads) | SEQ ID NO: 85 |
| C G A G C T G C C T : G C A G C A C C G G | 0.12% (6 reads) | SEQ ID NO: 86 |
| C G A G C T G C - - : - C A G A G C C G G | 0.12% (6 reads) | SEQ ID NO: 87 |
| C G G C T G C C T : G C A G A A C C G G | 0.12% (6 reads) | SEQ ID NO: 88 |
| G C G C T G C C [T] T : G C A G A G C C G G | 0.12% (6 reads) | SEQ ID NO: 89 | ically edits a mutant HD allele without inactivating all HTT protein.

SEQUENCE LISTING

```
<160> NUMBER OF SEQ ID NOS: 89

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
tgaagtgcac acagtggatg agg                                              23

<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2
gaagtgcaca cagtggatga ggg                                              23

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
tgaagtgcac acagtagatg agg                                              23

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
```
gaagtgcaca cagtagatga ggg                                          23

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
gaagtgcaca cagtagatga ggg                                          23

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
agggtttctt cgctcagcct tgg                                          23

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
gcccgagctg cctgcagaga accgg                                        25

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
gcccgagctg cctgcagagc cgg                                          23

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
tccagcccga gctgcctgca gag                                          23

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
gctcccgctc ggggttgatc tgg                                          23

<210> SEQ ID NO 11
<211> LENGTH: 23
<212> TYPE: DNA

```
<213> ORGANISM: Artificial Sequence
<220> FEATURE:
<223> OTHER INFORMATION: Synthetic

<400> SEQUENCE: 11
gcacatagag gatgccgtgc agg                                              23

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12
gcacatagag gacgccgtgc agg                                              23

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
catctactgt gtgcacttca                                                  20

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
cctcatccac tgtgtgcact tca                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
cctcatctac tgtgtgcact tca                                              23

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
gctccctcat ctactgtgtg                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gctccctcat ccactgtgtg                                                  20
```

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gctccctcat ccactgtgtg                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
gctccctcat ctactgtgtg                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
gctccctcat cctactgtgt                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: n is a, c, g, or t

<400> SEQUENCE: 21
gctccctcat cnactgtgtg                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is a, c, g, or t

<400> SEQUENCE: 22
gctccctcat ntactgtgtg                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)

```
<223> OTHER INFORMATION: n is a, c, g, or t

<400> SEQUENCE: 23
gctccctcnn ctactgtgtg                                           20

<210> SEQ ID NO 24
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(13)
<223> OTHER INFORMATION: n is a, c, g, or t

<400> SEQUENCE: 24
gctccctcat nnnctgtgtg                                           20

<210> SEQ ID NO 25
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is a, c, g, or t

<400> SEQUENCE: 25
gctccctcan ntactgtgtg                                           20

<210> SEQ ID NO 26
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is a, c, g, or t

<400> SEQUENCE: 26
gctccctcan ctactgtgtg                                           20

<210> SEQ ID NO 27
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(14)
<223> OTHER INFORMATION: n is a, c, g, or t

<400> SEQUENCE: 27
gctccctcat nnnntgtgtg                                           20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
```
gctccctcat gctactgtgt                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: n is a, c, g, or t

<400> SEQUENCE: 29
gctcccnnnt ctactgtgtg                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
gctccctcat cttactgtgt                                          20

<210> SEQ ID NO 31
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(20)
<223> OTHER INFORMATION: n is a, c, g, or t

<400> SEQUENCE: 31
gctccctcat nnnnnnnnnn                                          20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
tccctcatct ctactgtgtg                                          20

<210> SEQ ID NO 33
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 33
gctccnnnnn ctactgtgtg                                          20

<210> SEQ ID NO 34
<211> LENGTH: 20
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: n is a, c, g, or t

<400> SEQUENCE: 34
nnnnnnnnnn ctactgtgtg                                                    20

<210> SEQ ID NO 35
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(15)
<223> OTHER INFORMATION: n is a, c, g, or t

<400> SEQUENCE: 35
gctccctcat cnnnngtgtg                                                    20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
gctccctcat actactgtgt                                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(20)
<223> OTHER INFORMATION: n is a, c, g, or t

<400> SEQUENCE: 37
gctccctcan nnnnnnnnnn                                                    20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
gctccctcat ctactgtgtg                                                    20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
gctccctcat ccactgtgtg                                                    20
```

```
<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
gctccctcat ccactgtgtg                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
gctccctcat ctactgtgtg                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is a, c, g, or t

<400> SEQUENCE: 42
gctccctcan ntactgtgtg                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
gctccctcat cctactgtgt                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(14)
<223> OTHER INFORMATION: n is a, c, g, or t

<400> SEQUENCE: 44
gctccctcat nnnntgtgtg                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
```

```
<223> OTHER INFORMATION: n is a, c, g, or t

<400> SEQUENCE: 45
gctccctcnn ctactgtgtg                                                   20

<210> SEQ ID NO 46
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: n is a, c, g, or t

<400> SEQUENCE: 46
gctcccnnnt ctactgtgtg                                                   20

<210> SEQ ID NO 47
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(14)
<223> OTHER INFORMATION: n is a, c, g, or t

<400> SEQUENCE: 47
gctccctcan nnntgtgtg                                                    20

<210> SEQ ID NO 48
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is a, c, g, or t

<400> SEQUENCE: 48
gctccctcat ntactgtgtg                                                   20

<210> SEQ ID NO 49
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(13)
<223> OTHER INFORMATION: n is a, c, g, or t

<400> SEQUENCE: 49
gctccctcat cnnctgtgtg                                                   20

<210> SEQ ID NO 50
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (7)..(20)
<223> OTHER INFORMATION: n is a, c, g, or t

<400> SEQUENCE: 50
gctcccnnnn nnnnnnnnnn                                            20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
gctccctcct ccactgtgtg                                            20

<210> SEQ ID NO 52
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(16)
<223> OTHER INFORMATION: n is a, c, g, or t

<400> SEQUENCE: 52
gctccctcat nnnnnntgtg                                            20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gctccctcat cgctactgtg                                            20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gctccctcat ctactactgt                                            20

<210> SEQ ID NO 55
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(10)
<223> OTHER INFORMATION: n is a, c, g, or t

<400> SEQUENCE: 55
gctcccnnnn ctactgtgtg                                            20

<210> SEQ ID NO 56
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 56
gctccctcat ctaactgtgt                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
tccctcatct ctactgtgtg                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(20)
<223> OTHER INFORMATION: n is a, c, g, or t

<400> SEQUENCE: 58
gctccctcat nnnnnnnnnn                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gctccctcat aagctactgt                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(13)
<223> OTHER INFORMATION: n is a, c, g, or t

<400> SEQUENCE: 60
gctccctcat nnnctgtgtg                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 61
gctccnnnnn ctactgtgtg                                              20
```

<210> SEQ ID NO 62
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is a, c, g, or t

<400> SEQUENCE: 62
gctccctcan ctactgtgtg                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
gctccctcat agtactgtgt                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
cgagctgcct gcagaaccgg                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
cgagctgcct gcagagccgg                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
cgagctgcct gcagaaccgg                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
cgagctgcct gcagagccgg                                              20

<210> SEQ ID NO 68

```
<211> LENGTH: 20
<212> TYPE: DNA
<213> ORGANISM: Artificial Sequence
<220> FEATURE:
<223> OTHER INFORMATION: Synthetic

<400> SEQUENCE: 68
gagctgcctt gcagagccgg                                           20

<210> SEQ ID NO 69
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(8)
<223> OTHER INFORMATION: n is a, c, g, or t

<400> SEQUENCE: 69
cgagnnnnct gcagagccgg                                           20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
cgcgctgcct gcagaaccgg                                           20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
cgagctgcct gccgaaccgg                                           20

<210> SEQ ID NO 72
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: n is a, c, g, or t

<400> SEQUENCE: 72
cgagctnnnt gcagagccgg                                           20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
cgcgctgcct gcagagccgg                                           20
```

```
<210> SEQ ID NO 74
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: n is a, c, g, or t

<400> SEQUENCE: 74
cgannngcct gcagagccgg                                                   20

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
cgagctgcct gccgagccgg                                                   20

<210> SEQ ID NO 76
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is a, c, g, or t

<400> SEQUENCE: 76
cgagctgcct ncagagccgg                                                   20

<210> SEQ ID NO 77
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(9)
<223> OTHER INFORMATION: n is a, c, g, or t

<400> SEQUENCE: 77
cgagnnnnnt gcagagccgg                                                   20

<210> SEQ ID NO 78
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: n is a, c, g, or t

<400> SEQUENCE: 78
cgagctgcct nnagagccgg                                                   20

<210> SEQ ID NO 79
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 79
agctgcctgt gcagagccgg                                                    20

<210> SEQ ID NO 80
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is a, c, g, or t

<400> SEQUENCE: 80
cgagctgnct gcagagccgg                                                    20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
gagctgtgct gcagagccgg                                                    20

<210> SEQ ID NO 82
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is a, c, g, or t

<400> SEQUENCE: 82
cgagctgccn gcagagccgg                                                    20

<210> SEQ ID NO 83
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is a, c, g, or t

<400> SEQUENCE: 83
cgagctgncg gcagagccgg                                                    20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
agctgcctat gcagagccgg                                                    20
```

```
<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
cgagctgcct gcagaaccgc                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
cgagctgcct gcagcaccgg                                               20

<210> SEQ ID NO 87
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(11)
<223> OTHER INFORMATION: n is a, c, g, or t

<400> SEQUENCE: 87
cgagctgcnn ncagagccgg                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
cgggctgcct gcagaaccgg                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
gcgctgcctt gcagagccgg                                               20
```

ALLELE-SPECIFIC INACTIVATION OF MUTANT HTT VIA GENE EDITING AT CODING REGION SINGLE NUCLEOTIDE POLYMORPHISMS

PRIORITY STATEMENT

This application is a Non-Provisional application which claims benefit of U.S. Patent Provisional Application No. 63/136,378, filed on Jan. 12, 2021, of which is herein incorporated by reference in its entirety.

STATEMENT OF GOVERNMENT INTEREST

This invention was made with government support under R01NS106245 and UL1 TR000161-05 awarded by the NIH/NINDS and NIH, respectively. The government has certain rights in the invention.

SEQUENCE LISTING

A Sequence Listing has been submitted in an ASCII text file named "19981_ST25.txt," created on May 10, 2022 consisting of 19412 bytes, the entire content of which is herein incorporated by reference.

FIELD OF THE INVENTION

The present invention is related to gene therapy. In particular, the gene therapy provides gene editing of single nucleotide polymorphisms (SNP) using a CRISPR-Cas9 platform. For example, an SNP can be edited from a Huntingtin (HTT) gene to treat Huntington's disease. This treatment reduces the expression of the disease-causing mutated HTT protein without reducing the expression of the wild type HTT protein.

BACKGROUND

Huntington's disease (HD) is due to an autosomal dominant mutation in the huntingtin gene. In the mutant allele, a tandem CAG triplet repeat located in exon one is expanded to greater than 36 copies (Huntington's Disease Collaborative, 1993). The resulting polyglutamine (polyQ) peptide in the mutant huntingtin protein (mHTT) is considered the initiating pathogenic molecule (Aronin et al., 1995; DiFiglia et al., 1995; Huntingtons Disease Collaborative, 1993). A primary goal of conventional therapy is to reduce mHTT mRNA and protein (Sah and Aronin, 2011). Various strategies have been described to reduce HTT protein, including blocking transcription of the mutant gene (Garriga-Canut et al., 2012; Zeitler et al., 2019), and reducing mHTT mRNA using anti-sense oligonucleotides, siRNAs, viral-delivered miRNAs or transcriptional repressors (Alterman et al., 2019; Evers et al., 2018; Harper et al., 2005; Keeler et al., 2016; Kordasiewicz et al., 2012; Miniarikova et al., 2017; Pfister et al., 2018; Pfister et al., 2009; Stanek et al., 2014; Zeitler et al., 2019). These approaches have potential caveats. For example, translational repression with oligonucleotide therapies require multiple treatments and transcriptional inactivation requires persistent expression of an exogenous repressor.

While inactivation of a mutant HD allele offers a possible therapeutic approach for this disease, a permanent disruption of normal HTT function might compromise adult neuronal function. The present invention provides a gene editing platform that selectively edits a mutant HD allele without inactivating all HTT protein.

SUMMARY OF THE INVENTION

The present invention is related to gene therapy. In particular, the gene therapy provides gene editing of single nucleotide polymorphisms (SNP) using a CRISPR-Cas9 platform. For example, an SNP can be edited from a Huntingtin (HTT) gene to treat Huntington's disease. This treatment reduces the expression of the disease-causing mutated HTT protein without reducing the expression of the wild type HTT protein.

In one embodiment, the present invention contemplates a method, comprising: a) providing; i) a patient comprising a gene having a heterozygous allele pair associated with a genetic disease, wherein a first allele comprises a target sequence comprising a single nucleotide polymorphism (SNP) and a protospacer adjacent motif (PAM) and expresses a mutant protein and a second allele expresses a wild type protein; and ii) a composition comprising a Cas9 nuclease and an sgRNA molecule complex, wherein said sgRNA molecule targets said protospacer adjacent motif; and b) administering said composition to said patient under conditions such that said mutant protein expression is reduced and said wild type protein expression is unaffected. In one embodiment, the genetic disease is Huntington's disease. In one embodiment, the SNP flanks the PAM. In one embodiment, the SNP resides within the PAM. In one embodiment, said first allele comprises a mutated gene sequence that flanks said target sequence. In one embodiment said first allele further comprises a target sequence selected from the group consisting of SEQ ID NO; 1-12. In one embodiment, said mutant protein is a mutant Huntingtin protein. In one embodiment, said wild type protein is a wild type Huntingtin protein. In one embodiment, the sgRNA molecule hybridizes to said first allele. In one embodiment, the Cas9 nuclease edits said single nucleotide polymorphism to create a nonsense mutation. In one embodiment, said composition comprises a viral vector, wherein said viral vector encodes said Cas9 nuclease and said sgRNA molecule. In one embodiment, said viral vector is a lentivirus vector. In one embodiment, the viral vector is an adenovirus vector. In one embodiment, said composition comprises a plasmid molecule, said plasmid molecule encoding said Cas9 nuclease and said sgRNA molecule. In one embodiment, said Cas9 nuclease comprises a messenger ribonucleic acid molecule. In one embodiment, said Cas9 nuclease messenger ribonucleic acid molecule comprises a crRNA and a tracrRNA. In one embodiment, said Cas9 nuclease is a Cas9 protein. In one embodiment, said Cas9 protein is hybridized to an sgRNA. In one embodiment, said sgRNA comprises a crRNA and a tracrRNA.

In one embodiment, the present invention contemplates a method, comprising: a) providing; i) a patient exhibiting at least one symptom of a genetic disease; and ii) a composition comprising a Cas9 nuclease and an sgRNA molecule, wherein a portion of said sgRNA molecule is targeted to a gene comprising a single nucleotide polymorphism (SNP) that is in or near a protospacer adjacent motif and flanks a mutated nucleic acid sequence associated with said genetic disease; b) administering said composition under conditions such that expression of said at least one symptom is reduced. In one embodiment, said Cas9 nuclease edits said single nucleotide polymorphism to create a nonsense mutation. In one embodiment, the genetic disease is Huntington's disease. In one embodiment, the near SNP flanks said PAM. In one embodiment, the SNP flanks the PAM. In one embodiment, the SNP resides within the PAM. In one embodiment, the gene further comprises a target sequence selected from the group consisting of SEQ ID NO: 1-12. In one embodiment, said composition comprises a viral vector, wherein said Cas9 nuclease and said sgRNA molecule are encoded by said viral vector. In one embodiment, said viral vector is a lentivirus vector. In one embodiment, the viral vector is an adenovirus vector. In one embodiment, said composition comprises a plasmid molecule, said plasmid molecule encoding said Cas9 nuclease and said sgRNA molecule. In one embodiment, said Cas9 nuclease comprises a messenger ribonucleic acid molecule. In one embodiment, the Cas9 nuclease messenger ribonucleic acid molecule comprises a crRNA and a tracrRNA. In one embodiment, said Cas9 nuclease is a Cas9 protein. In one embodiment, the Cas9 protein is hybridized to an sgRNA. In one embodiment, the sgRNA comprises a crRNA and a tracrRNA.

In one embodiment, the present invention contemplates a method, comprising: a) providing; i) a gene encoding a mutated nucleic acid sequence associated with a genetic disease and a target sequence comprising a single nucleotide polymorphism (SNP) and a protospacer adjacent motif (PAM) and flanks said mutated nucleic acid sequence, and ii) a composition comprising a Cas9 nuclease and an sgRNA molecule, wherein said sgRNA molecule hybridizes to said target sequence; b) hybridizing said sgRNA molecule to said SNP; and c) editing said SNP with said Cas9 nuclease to create a nonsense mutation in said gene. In one embodiment, the genetic disease is Huntington's disease. In one embodiment, the SNP flanks the PAM. In one embodiment, the SNP resides within the PAM. In one embodiment, the mutated nucleic acid sequence is a mutated Huntingtin gene nucleic acid sequence. In one embodiment, the mutated Huntingtin gene nucleic acid sequence comprises a tandem CAG repeat expansion sequence. In one embodiment, the further comprises a target sequence selected from the group consisting of SEQ ID NO:'s 1-12. In one embodiment, the method further comprises administering said composition to a patient. In one embodiment, said composition comprises a viral vector, wherein said Cas9 nuclease and said sgRNA molecule are encoded by said viral vector. In one embodiment, said viral vector is a lentivirus vector. In one embodiment, the viral vector is an adenovirus vector. In one embodiment, said composition comprises a plasmid molecule, said plasmid molecule encoding said Cas9 nuclease and said sgRNA molecule, In one embodiment, said Cas9 nuclease is a messenger ribonucleic acid molecule. In one embodiment, said Cas9 nuclease messenger ribonucleic acid molecule comprises crRNA. In one embodiment, said Cas9 nuclease messenger ribonucleic acid molecule comprises tracrRNA. In one embodiment, said Cas9 nuclease messenger ribonucleic acid molecule comprises crRNA and tracrRNA. In one embodiment, said Cas9 nuclease is a protein.

In one embodiment, the present invention contemplates a composition comprising a Cas9 nuclease and an sgRNA molecule, wherein a portion of said sgRNA molecule is complementary to a target sequence comprising a single nucleotide polymorphism and a protospacer adjacent motif and flanks a mutated nucleic acid sequence associated with a genetic disease. In one embodiment, the SNP flanks the PAM. In one embodiment, the SNP resides within the PAM. In one embodiment, the gene coding sequence further comprises a target sequence selected from the group consisting of SEQ ID NOs: 1-12. In one embodiment, said composition comprises a viral vector, wherein said Cas9 nuclease and said sgRNA molecule are encoded by said viral vector. In one embodiment, said viral vector is a lentivirus vector. In one embodiment, the viral vector is an adenovirus vector. In one embodiment, said composition comprises a plasmid molecule, said plasmid molecule encoding said Cas9 nuclease and said sgRNA molecule, In one embodiment, said Cas9 nuclease is a messenger ribonucleic acid molecule. In one embodiment, said Cas9 nuclease messenger ribonucleic acid molecule comprises crRNA. In one embodiment, said Cas9 nuclease messenger ribonucleic acid molecule comprises tracrRNA. In one embodiment, said Cas9 nuclease messenger ribonucleic acid molecule comprises crRNA and tracrRNA. In one embodiment, said Cas9 nuclease is a protein.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein may be used to describe specific embodiments of the invention, but their usage does not delimit the invention, except as outlined in the claims.

The term "about" as used herein, in the context of any of any assay measurements refers to +/−5% of a given measurement.

As used herein, the term "CRISPRs" or "Clustered Regularly Interspaced Short Palindromic Repeats" refers to an acronym for DNA loci that contain multiple, short, direct repetitions of base sequences. Each repetition contains a series of bases followed by the same series in reverse and then by 30 or so base pairs known as "spacer DNA". The spacers are short segments of DNA from a virus and may serve as a 'memory' of past exposures to facilitate an adaptive defense against future invasions (PMID 25430774).

As used herein, the term "Cas" or "CRISPR-associated (cas)" refers to genes often associated with CRISPR repeat-spacer arrays (PMID 25430774).

As used herein, the term "Cas9" refers to a nuclease from CRISPR systems that may take the form of either a messenger ribonucleic acid (mRNA) comprising nucleic acids or a protein comprising amino acids. As a protein, Cas9 functions as an enzyme specialized for generating double-strand breaks in DNA, with two active cutting sites (the HNH and RuvC domains), one for each strand of the double helix. Jinek combined tracrRNA and spacer RNA into a "single-guide RNA" (sgRNA) molecule that, mixed with Cas9, could find and cleave DNA targets through Watson-Crick pairing between the guide sequence within the sgRNA and the target DNA sequence (PMID 22745249).

As used herein, the term "catalytically active Cas9" refers to an unmodified Cas9 nuclease comprising full nuclease activity.

The term "nickase" as used herein, refers to a nuclease that cleaves only a single DNA strand, either due to its natural function or because it has been engineered to cleave only a single DNA strand. Cas9 nickase variants that have either the RuvC or the HNH domain mutated provide control over which DNA strand is cleaved and which remains intact (Jinek, et al. 2012 (PMID 22745249) and Cong, et al. 2013 (PMID 23287718)).

The term, "trans-activating crRNA", "tracrRNA" as used herein, refers to a small trans-encoded RNA. For example, CRISPR/Cas (clustered, regularly interspaced short palindromic repeats/CRISPR-associated proteins) constitutes an RNA-mediated defense system, which protects against viruses and plasmids. This defensive pathway has three steps. First a copy of the invading nucleic acid is integrated into the CRISPR locus. Next, CRISPR RNAs (crRNAs) are transcribed from this CRISPR locus. The crRNAs are then incorporated into effector complexes, where the crRNA guides the complex to the invading nucleic acid and the Cas proteins degrade this nucleic acid. There are several pathways of CRISPR activation, one of which requires a tracrRNA, which plays a role in the maturation of crRNA. TracrRNA is complementary to base pairs with a pre-crRNA forming an RNA duplex. This is cleaved by RNase III, an RNA-specific ribonuclease, to form a crRNA/tracrRNA hybrid. This hybrid acts as a guide for the endonuclease Cas9, which cleaves the invading nucleic acid.

The term "protospacer adjacent motif" (or PAM) as used herein, refers to a DNA sequence that may be required for a Cas9/sgRNA to form an R-loop to interrogate a specific DNA sequence through Watson-Crick pairing of its guide RNA with the genome. The PAM specificity may be a function of the DNA-binding specificity of the Cas9 protein (e.g., a "protospacer adjacent motif recognition domain" at the C-terminus of Cas9).

The term "target sequence" as used herein, refers to a nucleic acid sequence capable of hybridizing with an sgRNA molecule as contemplated herein. In addition, a target sequence will include a protospacer adjacent motif (PAM). For example, a target sequence may include a single nucleotide polymorphism (SNP). The SNP may reside either within the PAM or in the part of the target sequence flanking the PAM.

The term "reside within the PAM" as used herein, refers to a SNP that is within the PAM DNA sequence.

The term "flanks a PAM" as used herein, refers to an SNP that is within twenty bases upstream of a PAM.

The term "flanks a mutated nucleic acid sequence" as used herein, refers to an sgRNA hybridizing to a target sequence that is within twenty bases of a mutated nucleic acid sequence.

As used herein, the term "sgRNA" refers to single guide RNA used in conjunction with CRISPR associated systems (Cas). sgRNAs are a fusion of crRNA and tracrRNA and contain nucleotides of sequence complementary to the desired target site (Jinek, et al. 2012); (PMID 22745249)). Watson-Crick pairing of the sgRNA with the target site permits R-loop formation, which in conjunction with a functional PAM permits DNA cleavage or in the case of nuclease-deficient Cas9 allows binds to the DNA at that locus.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "associated with" as used herein, refers to an art-accepted causal relationship between a genetic mutation and a medical condition or disease. For example, it is art-accepted that a patient having an HTT gene comprising a tandem CAG repeat expansion mutation has, or is a risk for, Huntington's disease.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "nonsense mutation" as used herein, refers to a point mutation in a sequence of DNA that results in the creation of a premature stop codon in the transcribed mRNA, that results in a truncated, incomplete, and usually nonfunctional protein product.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a sample, a compound or a sequence. In one respect, a sample, a compound or a sequence may be derived from an organism or particular species. In another respect, a sample, a compound or sequence may be derived from a larger complex or sequence.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that all trace impurities have been removed.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "truncated" as used herein, when used in reference to either a polynucleotide sequence or an amino acid sequence means that at least a portion of the wild type sequence may be absent. In some cases, truncated guide sequences within the sgRNA or crRNA may improve the editing precision of Cas9 (Fu, et al. 2014 (PMID 24463574)).

The term "base pairs" as used herein, refer to specific nucleobases (also termed nitrogenous bases), that are the building blocks of nucleotide sequences that form a primary structure of both DNA and RNA. Double stranded DNA may be characterized by specific hydrogen bonding patterns, base pairs may include, but are not limited to, guanine-cytosine and adenine-thymine) base pairs.

The term "specific genomic target" as used herein, refers to any pre-determined nucleotide sequence capable of binding to a Cas9 protein contemplated herein.

The term "cleavage" as used herein, may be defined as the generation of a break in the DNA. This could be either a single-stranded break or a double-stranded break depending on the type of nuclease that may be employed.

As used herein, the term "edit" "editing" or "edited" refers to a method of altering a nucleic acid sequence of a polynucleotide (e.g., for example, a wild type naturally occurring nucleic acid sequence or a mutated naturally occurring sequence) by selective deletion of a specific genomic target or the specific inclusion of new sequence through the use of an exogenously supplied DNA template. Such a specific genomic target includes, but may be not limited to, a chromosomal region, mitochondrial DNA, a gene, a promoter, an open reading frame or any nucleic acid sequence.

The term "delete", "deleted", "deleting" or "deletion" as used herein, may be defined as a change in either nucleotide or amino acid sequence in which one or more nucleotides or amino acid residues, respectively, are, or become, absent.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," may be complementary to the sequence "A-C-T-G." Complementarity can be "partial" or "total." "Partial" complementarity may be where one or more nucleic acid bases may be not matched according to the base pairing rules. "Total" or "complete" complementarity between nucleic acids may be where each and every nucleic acid base may be matched with another base under the base pairing rules. The degree of complementarity between nucleic acid strands has significant effects on the efficiency and strength of hybridization between nucleic acid strands. This may be of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which may be partially complementary, i.e., "substantially homologous," to a nucleic acid sequence may be one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This may be not to say that conditions of low stringency are such that non-specific binding may be permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be detected in a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which may be a "homolog" may be defined herein as an oligonucleotide sequence which exhibits greater than or equal to 50% identity to a sequence, when sequences having a length of 100 bp or larger are compared.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "allele" as used herein, refers to any one of a number of alternative forms of the same gene or same genetic locus.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide", refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and may be, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the term "hybridization" may be used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) may be impacted by such factors as the degree of complementarity between the nucleic acids, stringency of the conditions involved, the $T^m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0$ t or $R_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" may be used in reference to the "melting temperature." The melting temperature may be the temperature at which a population of double-stranded nucleic acid molecules becomes half dissociated into single strands. As indicated by standard references, a simple estimate of the $T_m$ value may be calculated by the equation: $T_m = 81.5 + 0.41(\% \text{ G}+\text{C})$, when a nucleic acid may be in aqueous solution at 1M NaCl. Anderson et al., "Quantitative Filter Hybridization" In: Nucleic Acid Hybridization (1985). More sophisticated computations take structural, as well as sequence characteristics, into account for the calculation of $T_m$.

As used herein the term "stringency" may be used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences may be usually low between such organisms).

As used herein, the term "amplifiable nucleic acid" may be used in reference to nucleic acids which may be amplified by any amplification method. It may be contemplated that "amplifiable nucleic acid" will usually comprise "sample template."

As used herein, the term "sample template" refers to nucleic acid originating from a sample which may be analyzed for the presence of a target sequence of interest. In contrast, "background template" may be used in reference to nucleic acid other than sample template which may or may not be present in a sample. Background template may be most often inadvertent. It may be the result of carryover, or it may be due to the presence of nucleic acid contaminants sought to be purified away from the sample. For example, nucleic acids from organisms other than those to be detected may be present as background in a test sample.

"Amplification" may be defined as the production of additional copies of a nucleic acid sequence and may be generally carried out using polymerase chain reaction. Dieffenbach C. W. and G. S. Dveksler (1995) In: PCR Primer, a Laboratory Manual, Cold Spring Harbor Press, Plainview, N.Y.

As used herein, the terms "restriction endonucleases" and "restriction enzymes" refer to bacterial enzymes, each of which cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring may be attached to the 3' oxygen of its neighbor in one direction via a phosphodiester linkage. Therefore, an end of an oligonucleotide may be referred to as the "5' end" if its 5' phosphate may be not linked to the 3' oxygen of a mononucleotide pentose ring. An end of an oligonucleotide may be referred to as the "3' end" if its 3' oxygen may be not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "bind", "binding", or "bound" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That may be typical when the binding component may be an enzyme and the analyte may be a substrate for the enzyme. Reactions resulting from contact between the binding agent and the analyte are also within the definition of binding for the purposes of the present invention.

BRIEF DESCRIPTION OF THE FIGURES

FIG. 1A-B presents an exemplary strategy for allele-specific targeting of mutant HTT protein by gene editing.

FIG. 1A: A strategy for allele-specific degradation of mutant Htt with SNP-specific nucleases. A schematic of the Htt gene depicts 3 of the 67 exons (not drawn to scale). Exon 1 can have a variable number of CAG repeats (indicated in the box labeled with Q, ex. Q18 & Q97). HD results when a single copy of the gene has a CAG repeat number greater than 36. To specifically alter the disease allele, an allele-specific gRNA-Cas9 nuclease targets a SNP that is heterozygous in an HD individual. In a mouse model of HD, the YAC18 transgene carries a normal version of the human HTT locus with the C allele of SNP RS362331 and the BAC97 transgene carries a mutant human HTT locus and the T allele of SNP RS362331. DNA cleavage and imprecise repair at the mutant HTT gene results in frameshift mutations that disrupt the coding region of the HD allele. Premature stop codons can reduce expression of the entire HTT protein, possibly through nonsense-mediated decay of the mature mRNA.

FIG. 1B. CRISPR-Cas9 target sequences specific for two alleles of exon 50 are shown. The heterozygous SNP is shown with a box. The PAM sequence is in bold.

FIG. 2A: A transfection assay tests the specificity of gRNA-Cas9 nucleases for the intended target sequence. A plasmid expressing the gRNA and Cas9 are co-transfected with a plasmid containing a target sequence between a direct repeat sequence that disrupts a GFP gene. Following transfection, target sequence cleavage followed by DNA repair creates an active GFP gene. GFP expression is quantified by FACS analysis and reflects the relative activity of a gRNA-Cas9 nuclease for the tested target sequence.

FIG. 2B: Reporter plasmids with the T and C target sequences for HTT Exon 50 SNP rs362331 were tested with the corresponding T and C gRNAs. A control guide and reporter target (mTet) has good activity when the guide has a GG PAM and decreased activity when the guide has an AG or CG PAM. The Y-axis indicates the percentage of transfected cells that expressed GFP.

FIG. 2C: Additional guides targeting SNPs in other exons were also tested.

FIG. 3A: Cartoon depicting the generation and infection of primary cortical neurons from mice heterozygous for YAC18 (wild type) and BAC97 (mutant) human transgenes as well as a Cas9 transgene.

FIG. 3B: An allele-specific sgRNA targeting the T allele of Htt Exon 50 (Ex50T) was introduced into BAC97/YAC18/Cas9 mouse primary neurons by lentiviral transduction using the LentiCRISPRcmvGFP vector. An sgRNA targeting the Rosa26 locus was used as a control. Genomic DNA was prepared 7 days following infection. PCR amplicons containing the targeted SNPs were barcoded and analyzed by Illumina sequencing. Insertion and deletion (InDel) allele frequencies were determined using the CRISPResso software package. The control sample has a higher frequency of the BAC97 allele than YAC18 due to a higher copy number of the BAC97 transgene. In the treated sample, 40% of reads are induced InDel mutations. N=3 mice and error bars represent the S.E.M. p-values less than 0.05 were considered significant.

FIG. 3C: The distribution of InDel sizes shows a strong bias towards frameshift mutations (filled bars) rather than in frame mutations (open bars). The insertion of a single base is the dominant allele type.

FIG. 4 shows exemplary data in the form of a mutation spectrum in BAC97/YAC18 mouse primary neurons. Distribution of the most frequent InDel alleles as determined by analysis with CRISPResso and SNPclassifier. Illumina sequences from samples described in FIG. 3A-C were analyzed using the CRISPResso sequence analysis program. Pinello et al., (2016). Sequences surrounding the targeted SNP sequence in HTT exon 50 are shown, with a dashed line indicating the cleavage site and an arrow indicating the SNP sequence (T or C). Inserted bases are indicated with a box and deleted bases are indicated with a hyphen. To the right of each sequence, read numbers are listed for the most commonly recovered sequences along with the size of the insertion or deletion (InDel). The SNP allele, as determined using SNPclassifier, is listed. SNPs whose allele was not determined (nd) are also indicated. A control sample (upper) was treated with a gRNA targeting the Rosa26 locus. In sequences from this sample, 81 percent of sequences had the T allele of the targeted SNP sequence while 18% have the non-targeted C allele. In sequences from the sample with a gRNA targeting the Exon 50 T allele (lower, Ex50Tg1), the C allele is now the most frequent sequence, followed by the T allele. The most frequent InDel mutation contains a single base insertion along with the sequence from the T allele of HTT exon 50. For the most frequently recovered mutations, the SNP had either the T allele or could not be determined.

FIG. 5A. Mutant HTT (mHTT) and normal HTT protein were assayed following treatment with sgRNAs targeting Exon 50 (Ex50Tg1) or a Rosa26 (control). mHTT is expressed from the BAC97 transgene and normal HTT protein is expressed from the YAC18 transgene. mHTT runs at a higher molecular weight due to the increased size of the poly Q repeat sequence (upper blot). Higher mHTT protein expression is observed because of the higher transgene copy number. Kalirin and beta-tubulin provide total protein concentration controls. The targeted mHTT protein, but not normal HTT protein, is reduced when targeted with sgRNA Ex50Tg1.

FIG. 5B. Quantification of HTT protein levels from digital images of the blot in A. mHTT and HTT signals are normalized to Kalirin levels. n=3. Error bars indicate the S.E.M.

FIG. 5C. An additional protein gel was overexposed to detect accumulation of truncated protein products corresponding to translational termination following frameshift mutations in exon 50.

FIG. 6A: Cartoon depicting the AAV vector used to deliver the Exon50Tg1 and control sgRNAs and the delivery of AAV to mouse brains. The HD model mice have two alleles at the exon50 SNP—the BAC97 transgene with the T allele and the YAC18Q transgene with the C allele. sgRNA Ex50Tg1 targets the T allele of the SNP heterozygosity. The gRNA and a turboRFP reporter gene are delivered by AAV injection into the adult mouse striatum in 8 week old animals. Cas9 activity is provided as a mouse transgene.

FIG. 6B: Analysis at multiple time points. At two, four and six weeks following AAV treatment, the frequency of the BAC97 allele is reduced and indel mutations are induced by the Ex50T programmed nuclease.

FIG. 6C: Analysis of flanking exons. Heterozygous SNPs were examined by Illumina sequencing at two flanking exons in the 4 weeks samples. There is no significant change in the ratio of BAC97 to YAC18 alleles in exons 48 or 57, indicating that cleavage and repair at exon 50 does not induce a high frequency of deletions large enough to remove these SNPs. N=3 mice and error bars represent the S.E.M.

FIG. 8A. Protein sample analysis of HTT and mHTT protein from the striatum of HD model mice with the Cas9, BAC97 and YAC18 transgenes. Each animal was bilaterally injected with AAV expressing the control (Rosa26) or Ex50Tg1 sgRNAs. Protein was isolated from striatal tissue. Vinculin serves as a total protein control. Signal is visualized as a virtual blot format.

FIG. 8B. Quantitative WES signals for mHTT and wild type HTT were normalized to vinculin. At both 4- and 6-weeks following injection with AAV expressing sgRNA Ex50T, mHTT was reduced by over 50% while wild type HTT was not significantly changed.

FIG. 9A: Western blot analysis of HTT and mHTT protein from the striatum of HD model mice with the Cas9, BAC97 and YAC18 transgenes. Each animal was bilaterally injected with AAV expressing the control (Rosa26) or Ex50Tg1 sgRNAs. Protein was isolated from striatal tissue. Vinculin represents the total protein control.

FIG. 9B. Western signals for mHTT and wild type HTT were quantified by digital imaging and normalized to Vinculin. At both 4- and 6-weeks following injection with AAV expressing sgRNA Ex50T, mHTT was reduced by over 50% while wild type HTT was not significantly changed. N=3 mice and error bars represent the S.E.M. p-values less than 0.05 were considered significant.

FIG. 10A-D presents exemplary data showing the absence of detectable mHTT truncation proteins after editing at exon 50.

FIGS. 10A-10D: Full sized Western blot images prepared from the same samples and overexposed to detect lower abundance protein products. No protein signal was observed that represented a truncated HTT protein.

FIG. 11A: Protein simple analysis detected DARRP-32, a marker of neuronal identity, and GFAP, a marker of activated glial cells.

FIG. 11B. Quantification of signals from panel A did not detect significant changes at 4 or 6 weeks following injection. Protein levels were normalized to signal for vinculin protein. N=3 mice and error bars represent the S.E.M. p-values less than 0.05 were considered significant.

FIG. 12A: Immunostaining of an adult mouse brain section with anti-turbo RFP illustrates the unilateral spread of the injected scAAV throughout the striatum.

FIG. 12B: Immunostaining with anti-IBA-1 measures glial cells that are activated following neurotoxic stress. Overall IBA-1 staining is not increased in the injected hemisphere.

FIG. 12C: A closer view of anti-IBA-1 stained sections reveals that activated glia are only visible directly adjacent to the needle track (right panel), suggesting a response to mechanical damage.

FIG. 12D: The number of resting and activated IBA-1 positive glia are unchanged following AAV injection and editing.

FIG. 12E: The number of DARRP-32 positive neurons is unchanged following AAV injection and editing.

FIG. 13A. The relative copy number of human exon 50 was measured using primers (arrows with dashes between them) and a probe (arrow below primer) flanking the CRISPR-Cas9 target site. A second set of primers and probe (arrow below primer)) were used to determine the copy number of a reference locus, the mouse RPP30 gene.

FIG. 13B: Following DNA cleavage and repair, ddPCR detects chromosomes with either of the original SNP allele sequences or small insertion/deletion (InDel) alleles.

FIG. 13C: ddPCR does not detect chromosomes with mutations that either remove (large deletions) or separate (translations or large insertions) the primer binding sites.

FIG. 13D: ddPCR was used to determine the total copy number of transgenic human HTT exon 50 in the primary neurons using the mouse RPP30 as a reference for the diploid genome. Samples were treated with lentivirus expressing Ex50T gRNA or a control (Rosa26) gRNA. Exon 50 copy number was decreased from an average of 10.2 to 5.7 across three paired neuronal samples. The 44% reduction reflects alleles that can no longer be amplified using the primers for allele sequencing.

FIG. 13E: The fraction of each allele class is estimated by multiplying the fraction of sequenced alleles by the estimated fraction of alleles that could be amplified (0.56) based on the ddPCR results. "non-amp" indicates the estimated fraction of alleles that could not be amplified. FIG. 13F: ddPCR was used to determine the total copy number of human HTT exon 50 in the four-week striatal samples treated with AAV expressing the Ex50T or a control (Rosa26) gRNA and in untreated tail DNA from the same animals. There was no significant difference in the exon 50 copy number between tails and striatum treated with the control gRNA. In contrast, the copy number was reduced by an average of 36% in striatum treated the Ex50T gRNA. This reduction reflects alleles that can no longer be amplified using the primers for allele sequencing. FIG. 13G: The fraction of each allele class is estimated by multiplying the fraction of sequenced alleles by the estimated fraction of alleles that could be amplified (0.64) based on the ddPCR results. "non-amp" indicates the estimated fraction of alleles that could not be amplified.

FIG. 14A: Lentiviral insertions at genomic editing target sites. Striatal samples were treated with lentivirus expressing gRNAs that target human Htt Exon 50T or a control locus, Rosa26. To determine if some alleles contain viral insertions at the target site, PCR was performed with a primer that recognizes the long terminal repeat (LTR1) and a primer upstream (Ex50_F) or downstream (Ex50_R) of the target site. Products were only observed in samples with editing at HTT exon 50.

FIG. 14B: AAV insertions at genomic editing target sites. Striatal samples were treated with AAV expressing gRNAs that target human Htt Exon 50T or a control locus, Rosa26. To determine if some alleles contain AAV insertions at the target site, PCR was performed with a primer that recognizes the inverted terminal repeats of AAV (AAV-ITR) and a primer upstream (Ex50_F) or downstream (Ex50_R) of the target site. Products were only observed in samples with editing at HTT exon 50. Similarly, primers designed to detect insertions at the control locus (AAV-ITR with Rosa26_F or Rosa26_R) only produced products in samples with editing at the mouse Rosa26 locus.

FIG. 15 presents exemplary data showing allele-specific induction of InDels in heterozygous HD fibroblasts. HD patient fibroblasts were treated with lentivirus expressing allele-specific sgRNAs and Cas9 and analyzed by Illumina sequencing. The nuclease cleavage site and SNP heterozygosity are indicated with arrows. The non-targeted allele is highlighted in bold. Insertions (red outline), deletions (dashes) and substitutions (bold) are indicated. In the control cells (top), the allele frequency is roughly equal. (Note, the total is slightly less than 100% because substitution mutations due to PCR or sequencing errors are not shown).

DETAILED DESCRIPTION OF THE INVENTION

Figure 1A:
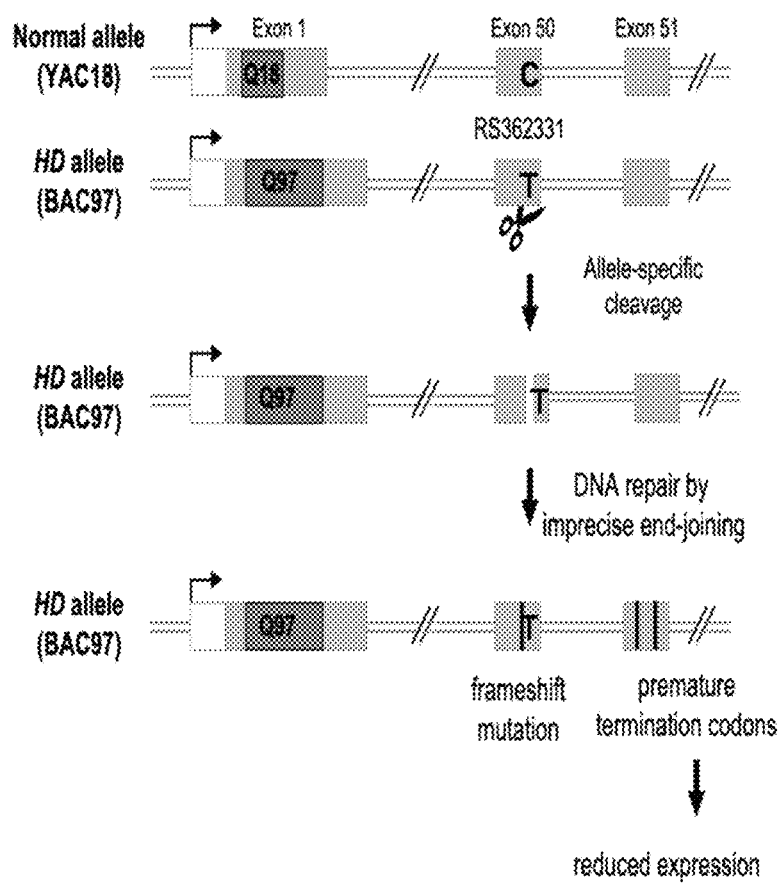

The present invention is related to gene therapy. In particular, the gene therapy provides gene editing of single nucleotide polymorphisms (SNP) using a CRISPR-Cas9 platform. For example, an SNP can be edited from a Huntingtin (HTT) gene to treat Huntington's disease. This treatment reduces the expression of the disease-causing mutated HTT protein without reducing the expression of the wild type HTT protein.

In one embodiment, the present invention contemplates allele-specific gene editing based on targeting a heterozygous single nucleotide polymorphism (SNP) in the HTT protein coding sequence, but the SNP flanks the mutated tandem CAG repeat HTT coding sequence responsible for the genetic disease. The data shown herein demonstrates that the outcome of such gene editing is a marked and selective reduction of mutant HTT (mHTT) protein expression in a mouse model of HD. Expression of a single CRISPR-Cas9 nuclease in neurons generated a high frequency of mutations in the targeted HD allele that included both small insertion/deletion mutations (InDels) and viral vector insertions. Thus, as disclosed herein, allele-specific targeting of InDel and insertion mutations to heterozygous coding region SNPs provides a feasible approach to inactivate autosomal dominant mutations that cause genetic disease without genetic manipulation of the mutated gene sequence associated with the genetic disease.

Although it is not necessary to understand the mechanisms of an invention, it is believed that inactivation of a mutant HTT gene (e.g., reducing mutant HTT protein expression) relies on editing of single coding region SNPs. As detailed below, the prior art proposes targeting two SNPs to create large deletion alleles. However, these approaches are limited by the high frequency of indel or viral insertion mutations at the individual sites. In one embodiment, the present invention contemplates targeting a single SNP within a coding region of a mutant HTT that is sufficient to prevent expression of the mutant protein, wherein the SNP flanks the mutated tandem CAG repeat gene sequence associated with HTT. It is further believed that editing a single coding region SNP disrupts mutant HTT protein expression in a sufficient number of neurons to prevent development of HD.

I. Huntington's Disease

Huntington's disease (HD) is a fully penetrant neurodegenerative disease believed to be caused by a dominantly inherited CAG trinucleotide repeat expansion in the huntingtin gene on chromosome 4. In Western populations HD has a prevalence of 10.6-13.7 individuals per 100 000. It is characterized by cognitive, motor and psychiatric disturbance. At the cellular level mutant huntingtin results in neuronal dysfunction and death through a number of mechanisms, including disruption of proteostasis, transcription and mitochondrial function and direct toxicity of the mutant protein. Early macroscopic changes are seen in the striatum with involvement of the cortex as the disease progresses. There are currently no disease modifying treatments; therefore supportive and symptomatic management is the mainstay of treatment. In recent years, there have been significant advances in understanding both the cellular pathology and the macroscopic structural brain changes that occur as the disease progresses. In the last decade there has been a large growth in potential therapeutic targets and clinical trials. Perhaps the most promising of these are the emerging therapies aimed at lowering levels of mutant huntingtin. Antisense oligonucleotide therapy is one such approach with clinical trials currently under way. McColgan et al., "Huntington's Disease: A Clinical Review" Eur J Neurol 25(1): 24-34 (2018).

HD is due to an autosomal dominant mutation in the first exon of the huntingtin gene (HTT). HD patients have a mutant HTT (mHTT) with an expansion of a tandem CAG repeat to greater than 36. The mode for the expansion number is 42 (Snell et al., 1993). The presentation of HD can be subsumed in three categories: cognitive impairment, depression and movement disorder (chorea or stiffness). The disease in the adult form often begins at about 30 to 40 years of age, with much variability. A juvenile form (associated with 60 or more CAG repeats) is characterized by stiffness of movement; the course extends to at least one decade of survival, but the patient often receives medical care in a long-term facility for much of the duration.

The mutant huntingtin protein (mHTT) is considered the initiating pathogenic molecule; the mRNA containing increased CAG repeats may also contribute. Snell et al., (1993); Aronin et al., {1995); Didiot et al., (2018); and Veitch et al., (2007). A primary goal of therapy is to reduce mHTT mRNA and protein. Sah and Aronin, (2011). Various strategies have been described to reduce HTT protein: blocking transcription of mHTT. Garriga-Canut et al., (2012), reducing mHTT mRNA using anti-sense oligonucleotides, siRNAs or viral-delivered miRNAs. Harper et al., (2005); Keeler et al., (2016); Kordasiewicz et al., (2012); Pfister et al., (2018); and Pfister et al., (2009). Each of these approaches have potential drawbacks. For example, oligonucleotide delivery requires multiple treatments and the degree of off-target effects for RNA targeting approaches is difficult to assess.

A known problem in the art is the lack of therapeutics for autosomal dominant disorders such as HD that reduce the activity of the mutant protein while preserving normal protein function. Herein, the usefulness of CRISPR-Cas gene editing at a protein coding region SNP with high heterozygosity in the HD population is demonstrated to solve that problem. Previous studies have targeted SNPs to make deletions of mutant HTT exon 1 in HD fibroblasts or HD model mice. Monteys et al., (2017); Shin et al., (2016); Yang et al., (2017). A possible limitation of these past approaches is the efficiency of generating deletions in vivo; when two target sites for gene editing are not close, the frequent induction of viral insertions or InDel mutations at one or both sites will prevent the formation of deletions between the two sites. Nelson et al., (2019). In contrast, when targeting single SNP heterozygosities that occur within the protein coding region, either individual InDel mutations or other mutations such as large insertions or deletions are sufficient to reduce protein levels. The presently disclosed results targeting a single coding region SNP heterozygosity demonstrates a high efficiency of allele-specific reduction of the targeted gene. Multiple coding region SNPs with high heterozygosity rates in HD patients have been reported. Pfister et al., (2009). Consequently, the presently contemplated methods of treating HD are believed to be applicable to a majority of HD patients.

An unexpected outcome of the present invention was the increase in the percentage of sequence reads with the non-targeted allele in treated neurons (the YAC18 allele). In dividing cells, this increase could reflect homology-dependent repair of the targeted allele using the non-targeted allele as a donor. However, homology-dependent repair is low or absent in most post-mitotic cells such as neurons. It found that most induced mutations were excluded from a sequence analysis due to a lack of amplification. When these "unamplifiable" alleles were added to the amplified and sequenced alleles, the non-targeted alleles were unchanged after gene editing.

Recent studies suggest that a combination of AAV vector insertions, large deletions or other rearrangements can comprise a major fraction of edited alleles when AAV is used to deliver gene editing components. Hanlon et al., (2019); Mccullough et al., (2019); Nelson et al., (2019). As shown herein, most mutations induced by AAV or by lentivirus delivery of sgRNAs were not amplified using primers that flank the targeted site. With both AAV and lentivirus, the viral vector sequences were found at the CRISPR-Cas9 targeted site. These results suggest that many gene editing reports using either lentivirus or AAV may have a potential bias for frequent viral insertions at the targeted site. While AAV and integrase-defective lentivirus were known to insert at sites of induced DNA breaks, the data presented herein indicate that integrase-competent lentivirus is also targeted to induced DNA breaks. Depending on the types of sequences carried by the viral vector, such insertions might result in a different cellular outcome than would be expected with a simple InDel or deletion allele.

The terminal regions of both viral vectors are believed to have stop codons in all three reading frames. When these sequences insert at the exon 50 editing site, they are predicted to result in a truncated mHTT protein coding region. For the HTT locus, it is demonstrated that while there are both the expected InDel mutations and unanticipated viral insertions, the outcome of editing at the exon 50 SNP is a significant reduction in full length HTT protein and no detectable truncated products. These results suggest that either InDel or insertion mutations result in altered RNA and/or protein products with reduced expression. It is concluded that using viral delivery to target coding region SNPs for gene editing is a viable approach to selectively reduce mutant HTT protein expression without affecting wild type HTT protein expression.

II. Cas9 Single Polymorphism Nucleotide Editing Platforms

The CRISPR-Cas9 protein complex has been reported to be an effective platform for gene editing. Heidenreich and Zhang, (2016); Hsu et al., (2014). In one embodiment, the present invention contemplates a CRISPR-Cas9 complex designed to permanently prevent expression of a toxic mHTT protein. The CRISPR-Cas9 nuclease complex is typically composed of a single guide RNA (sgRNA) that pairs with DNA and a multifunctional Cas9 protein that binds a short DNA sequence that cleaves a target DNA site. Such systems have been used to induce double strand DNA breaks, whose processing by cellular DNA end-joining repair pathways can disrupt protein expression by generating small frameshift mutations at single target sites or large deletions between pairs of sites.

While gene editing has been suggested as useful for HD treatment, it is generally known that several significant limitations and disadvantages needed to be addressed and solved. Merienne et al., (2017); Yang et al., (2017). For example, given the permanent nature of DNA sequence changes and the essential role of HTT in brain function, normal HTT activity needs to be retained following any HD treatment. Burrus et al., (2020); Dragatsis et al., (2000); Liu and Zeitlin, (2017); Mckinstry et al., (2014); Mehler et al., (2019). It has been reported that allele-specific targeting of HTT using CRISPR-Cas9 based nucleases can distinguish between single nucleotide polymorphism (SNP) target sites. Monteys et al., (20170; Shin et al., (2016); Yang et al., (2017). These studies, however, are not useful for clinical treatment because they used nucleic acid targets that are infrequently polymorphic or create large deletions that may not be efficiently generated in vivo. In one embodiment, the present invention solves these problems in the art by disclosing a gene editing strategy to prevent expression of mHTT by using the single nucleotide specificity of CRISPR-Cas9 gene editing to target common SNP heterozygosities in the HTT coding region and block mHTT expression. See, FIG. 1A-B.

The CRISPR-Cas9 nuclease complex is composed of a single guide RNA (sgRNA) that base pairs with DNA and the Cas9 protein that binds a short protospacer adjacent motif (PAM) sequence and cleaves the target DNA site. Processing of these breaks by end joining DNA repair pathways can inactivate mammalian genes by introducing frameshift mutations or large deletions that prevent generation of functional protein. Analysis of CRISPR-Cas9 nuclease specificity indicates that some single base mutations in the target sequence can strongly reduce target cleavage by the nuclease while other mismatches have little or no effect on cleavage. Hsu et al., (2013). While direct and permanent inactivation of the disease-causing mHTT gene (e.g., tandem CAG repeat sequences) is appealing, several caveats create potential obstacles. Given conflicting results regarding the essential role for HTT protein in the mouse brain, it is prudent to retain the wild type HTT protein, especially since animals models may not capture essential, long-term role in the human brains. Liu and Zeitlin, (2017); and Wang et al., (2016). Thus, gene editing should efficiently reduce mutant HTT protein without disrupting wild type HTT protein.

In one embodiment, the present invention contemplates a gene editing strategy to reduce and/or prevent expression of mutant HTT protein (mHTT) using the single nucleotide specificity of gene editing to block mHTT expression by targeting individual SNP heterozygosities in the HTT coding region that flank the tandem CAG repeat expansion sequences.

A. Targeting HTT SNP Heterozygosities with Allele-Specific Nucleases

In one embodiment, the present invention contemplates a CRISPR-Cas9 complex to selectively reduce and/or prevent expression of the mHTT protein while retaining expression of a wild type HTT protein. Although it is not necessary to understand the mechanism of an invention, it is believed that the presently disclosed CRISPR-Cas9 allele-specific targeting is based on discrimination between HTT coding region SNPs that are heterozygous between two alleles. This is in contrast to previous allele-specific editing strategies targeting SNPs that flank an exon or make large deletions in the gene. Merienne et al., (2017); Monteys et al., (2017); Shin et al., (2016); Vachey and Deglon, (2018); Yang et al., (2017). The prior art utilizes two cut sites which can limit the efficiency of mHTT disruption since InDel mutations or viral vector insertions at each target site will compete with deletions between both target sites. Hanlon et al., (2019); Mccullough et al., (2019); Nelson et al., (2019). These studies have utilized single nucleotide polymorphism (SNP) target sites that are either rarely polymorphic in HD patients or that create large deletions that may not be efficiently generated in vivo. Of particular concern, recent studies have demonstrated that insertion of viral genomes used to deliver the editing components can comprise a high frequency of the events at a given target site. These insertion alleles will potentially compete with the production of deletions intended to inactivation mHTT.

As disclosed herein, the present invention contemplates targeting single coding SNP sites that have high heterozygosity rates in HD patients. Pfister et al., (2009). Although it is not necessary to understand the mechanism of an invention, it is believed that that CRISPR-Cas9 induced frameshift mutations in protein coding regions can evoke cellular mRNA surveillance mechanisms that block or reduce expression of the resulting protein. Popp and Maquat, (2013).

Figure 2A:
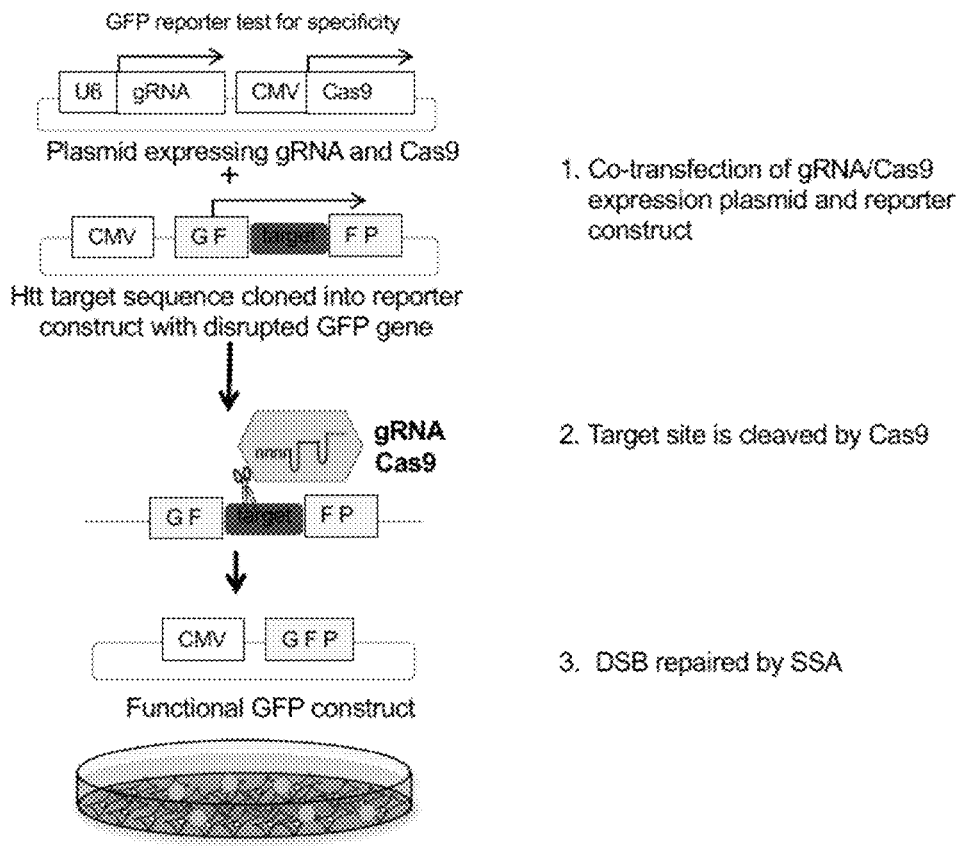
FIG. 2A-C presents exemplary data showing the discrimination of two alleles of Htt by CRISPR-Cas9 based nucleases.
Figure 2B:
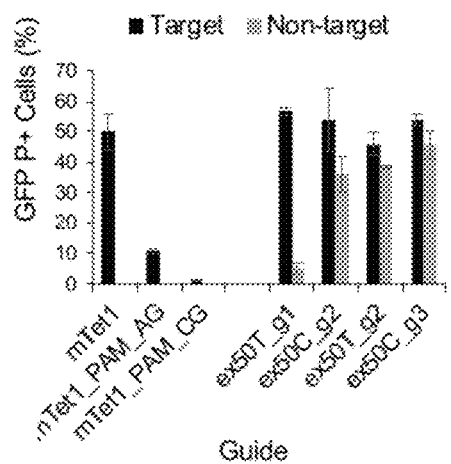
Figure 2C:
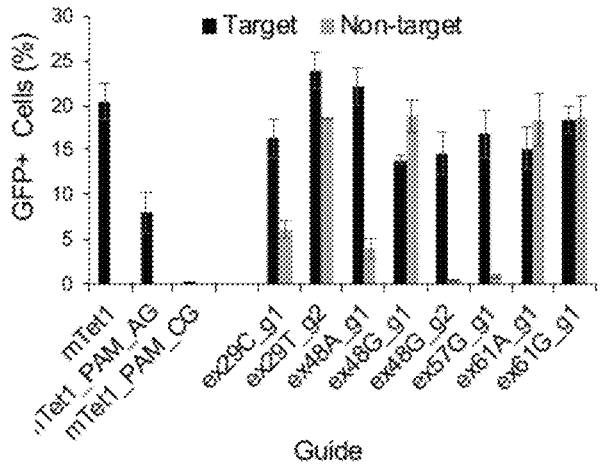

A computational tool (CRISPRseek) predicts the difference in cleavage activity between a perfect target site (e.g. the targeted SNP allele) or a mismatched target site (e.g. the non-targeted allele). Zhu et al., (2014). For example, an allele-specific example is diagrammed where an sgRNA is designed to target the "T" allele of a SNP heterozygosity in exon 50. See, FIG. 1A-B. The non-targeted "C" allele has a mismatch to the hybridizing sgRNA. A GFP reporter assay was used to test candidate nucleases that have high activity for the targeted SNP allele and little or no activity for the other allele. Wilson et al., (2013); See, FIG. 2A-C. Each gRNA sequence was tested for allele-specificity using reporters with the targeted and non-targeted allele sequences. gRNAs targeting SNPs in exons 48, 50 and 57 have high specificity for the targeted allele. Candidate allele-specific target sequences for coding sequence SNPs in the human huntingtin gene have been identified. SNPs were targeted in Exons 29, 48, 50, 57 and 61. Selected target sites all have the SNP heterozygosity in or near the PAM sequence. The SNP is indicated within boxes and the PAM sequence is indicated in bold. All guides have an NGG PAM except for Ex48G_g2 which has a NAG PAM. See, Table I.

B. Reduction of Mutant HTT Protein Expression

CRISPR-Cas9 gene editing at protein coding region SNPs was tested for allele-specific reduction and/or blockage of mHTT protein in neurons. Unlike mutations in gene flanking regions, intronic or UTR regions, a single frameshift mutation in the coding region could disrupt (e.g., reduce or inactivate) gene expression by nonsense-mediated decay of mRNA. An Ex50T-g1 gRNA was used to target the T allele of SNP RS362331 in exon 50. The RS362331 SNP was chosen for proof of principle because this SNP is the most frequently heterozygous protein coding region SNP in HD patients and the T allele is more frequently present on the mutant HTT gene allele. Pfister et al., (2009); and Chao et al., (2017).

Figure 3A:
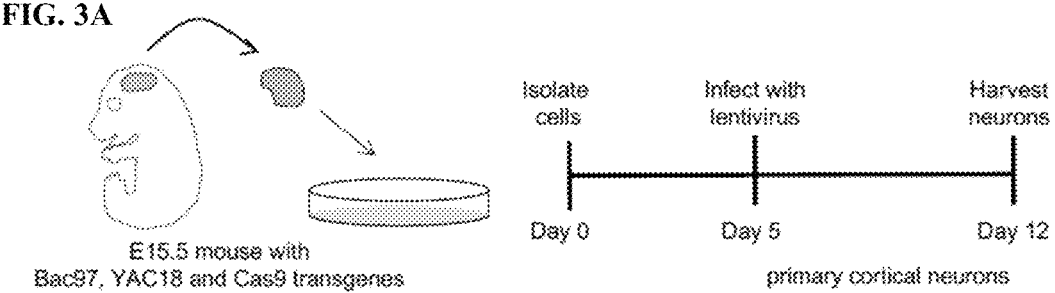
FIG. 3A-C presents exemplary data shown CRISPR-Cas9 allele-specific targeting of mHTT in BAC97/YAC18 primary neurons.
Figure 3B:
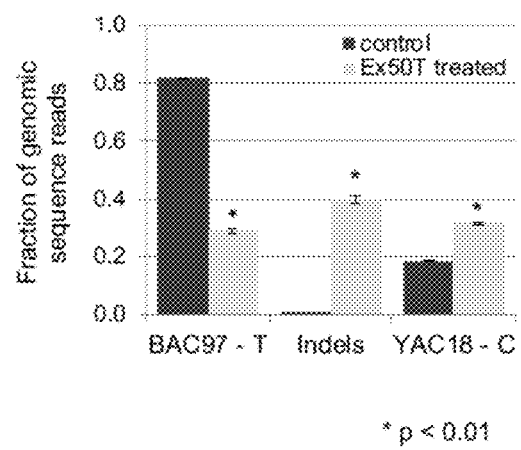
Figure 3C:
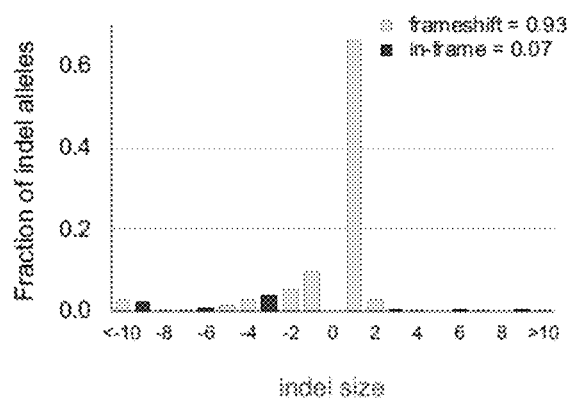

Primary cortical neurons were derived from a mouse model with heterozygosity for normal and mutant human HTT. See, FIG. 3A-C. The BAC97 transgene encodes a mHTT protein with 97 glutamine codons and has the "T" allele at the exon 50 SNP. Gray et al., (2008). The YAC18 transgene expresses normal HTT and has the "C" allele at exon 50. Hodgson et al., (1999). The mice were also homozygous for a null mutation of the endogenous mouse HTT gene and expressed transgenic Cas9. Zeitlin et al., (1995); Platt et al., (2014). An sgRNA targeting the T allele at exon 50 (Ex50T) was delivered to primary neurons by lentiviral transduction 5 days after isolation and cells were harvested one week later. See, FIG. 3A. An sgRNA targeting the mouse Rosa26 locus was used as a control.

Edited genomic DNA sequences from the exon 50 SNP region were determined by Illumina sequencing of PCR amplicons. In control samples, the "T" allele present in the BAC97 transgene was present in 81% of sequences and the C allele from the YAC18 transgene was present in 19%, reflecting a higher copy number for the BAC97 transgene. See, FIG. 3B. In Ex50Tg1 treated neurons, sequences with the unaltered "T" allele were reduced from 81% to 29%, while sequences harboring induced insertion/deletion (InDel) mutations rose to 40%, suggesting that the InDel

TABLE 1

Candidate allele-specific target sequences for coding sequence SNPs in the human huntingtin gene

Figure 4:
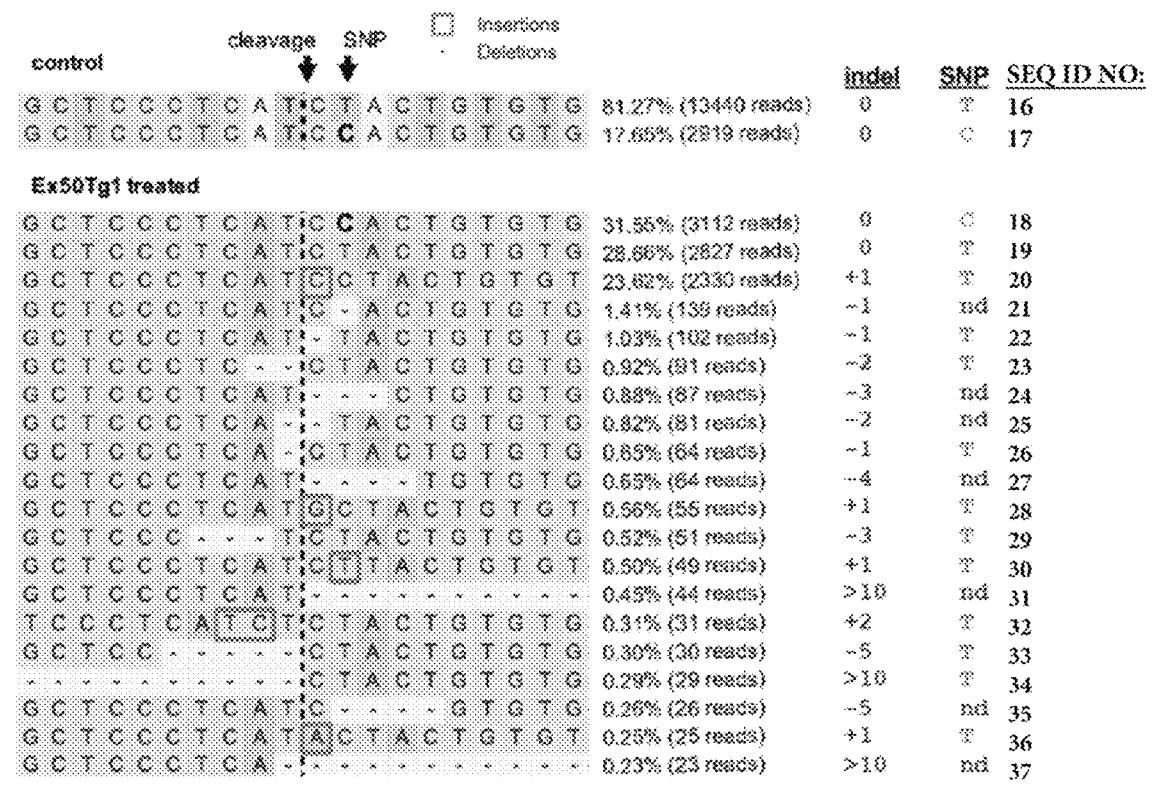

| Guide Name | GuidePlusPAM | Position | SNP Identification Number | % Heterozygous in HD |
|---|---|---|---|---|
| Ex50C_g2 | TGAAGTGCACACAGTGGATGAGG | Exon 50 | rs362331 | 39.4 |
| Ex50C_93 | GAAGTGCACACAGTGGATGAGGG | | | |
| Ex50T_g1 | TGAAGTGCACACAGTAGATGAGG | | | |
| Ex50T_g2 | GAAGTGCACACAGTAGATGAGGG | | | |
| Ex29C_g1 | GAAGTGCACACAGTAGATGAGGG | Exon 29 | rs4690074/rs363099 | 35.8 |
| Ex29T_g2 | AGGGTTTCTTCGCTCAGCCTTGG | | | |
| Ex48A_g1 | GCCCGAGCTGCCTGCAGAACCGG | Exon 48 | rs4690077 | 37.4 |
| Ex48G_g1 | GCCCGAGCTGCCTGCAGAGCCGG | | | |
| Ex48G_g2 | TCCAGCCCGAGCTGCCTGCAGAG | | | |
| Ex57G_g1 | GCTCCCGCTCGGGGTTGATCTGG | Exon 57 | rs362273 | 35.2 |
| Ex61A_g1 | GCACATAGAGGATGCCGTGCAGG | Exon 61 | rs362272 | 36.1 |
| Ex61G_g1 | GCACATAGAGGACGCCGTGCAGG | | | | mutations result from inaccurate repair of DNA breaks at the targeted "T" allele. Analysis of individual sequences predicts that most induced mutations will truncate the predicted coding region of the mutant HTT gene. See, FIG. 3C; and FIG. 4; and Pinello et al., (2016). The data show that greater than 90% of the observed InDel mutations are frameshift mutations with the most frequent allele being the addition of a single C nucleotide at the cleavage site.

The above data shows that nearly all induced mutations arose from the targeted "T" allele by examining the identity of the SNP within these sequences. For most InDel mutations, the polymorphic base from SNP RS362331 is still present, allowing the InDel to be attributed to one of the two parental alleles. For example, the single C insertion is associated with the T allele of the SNP. See, FIG. 4 (Ex50Tg1 treated, third line). In contrast, the provenance of some alleles cannot be determined due to deletion of the diagnostic SNP. See, FIG. 4 (Ex50Tg1 treated, seventh line). A custom software tool (e.g., SNPclassifier) assigned all alleles either to the parental T allele, or the parental C allele, or to an undetermined category. The majority of InDel mutations in primary neurons treated with the Ex50T gRNA were either associated with the parental T allele or not determined. The frequency of InDel mutations induced on targeted and non-targeted HTT SNP alleles in CRISPR-Cas9 treated HD fibroblasts and mouse neurons. See, Table 2.

TABLE 2

Frequency of InDel mutations in HTT SNP Alleles[1]

| Cell type | Neuron | Fibroblast | Fibroblast |
|---|---|---|---|
| sgRNA | Ex50Tg1 | Ex50Tg1 | Ex48Gg2 |
| Total Reads | 9836 | 25168 | 92458 |
| Indels - target SNP allele | 3052 | 1928 | 11766 |
| Indels - non-target SNP allele | 7 | 3 | 13 |
| Indels - not determined | 3059 | 2272 | 327 |
| Ratio target/non-target | 436 | 643 | 905 |

[1]Illumina sequencing was analyzed using a combination of CRISPResso and SNP classifier software.

Figure 5A:
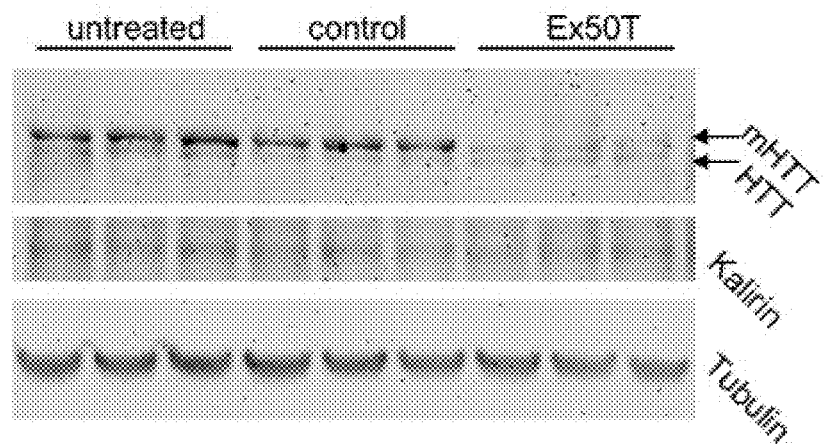
FIG. 5A-C presents exemplary data showing allele-specific reduction of mutant HTT protein in primary neurons from a HD mouse using a CRISPR-Cas9 platform.
Figure 5B:
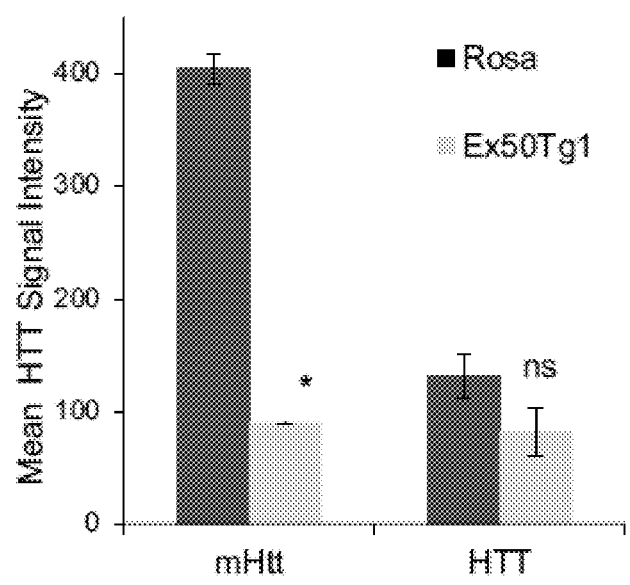
Figure 5C:
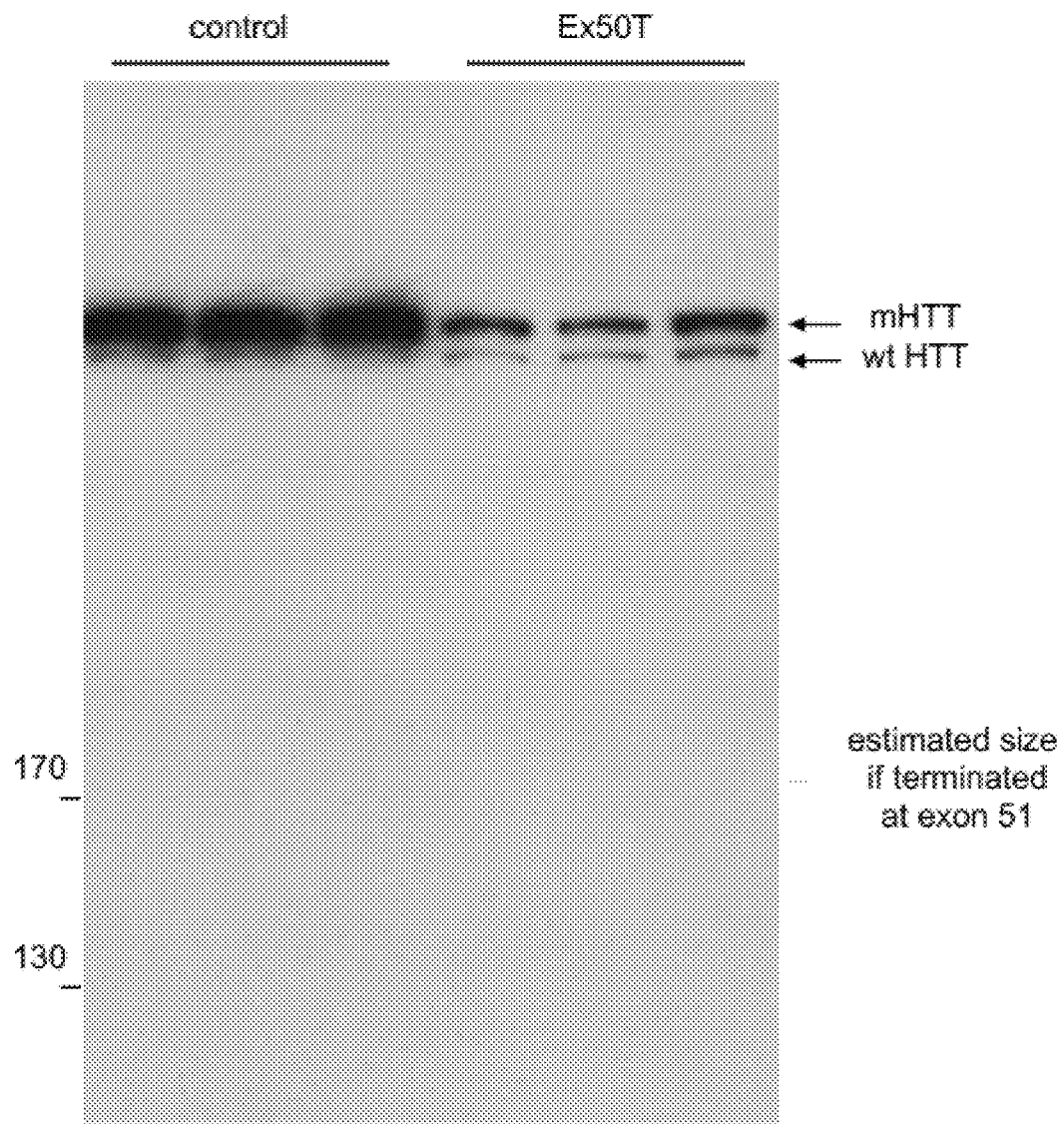

In one embodiment, the present invention contemplates allele-specific editing that reduces mutant HTT protein expression while unaffecting (e.g., maintaining) wild type HTT protein expression. The data presented herein demonstrates that the presently disclosed CRISPR-Cas9 gene editing platform reduced full length mutated HTT (mHTT) protein (BAC97) expression with no detectable change in the wild type HTT protein (YAC18) expression. See, FIGS. 5A, 5B. Although the frameshift mutations introduced by gene editing in exon 50 create premature stop codons in exon 51, the corresponding smaller HTT protein fragments were not detected by Western blot analysis. See, FIG. 5C. Thus, the present data demonstrates that allele-specific targeting of HTT using the presently disclosed CRISPR-Cas9 complexes in primary neurons resulted in selective reduction of mutant HTT protein expression, but not wild type HTT protein expression.

C. Gene Editing at SNP Heterozygosities Selectively Lowers mHTT Protein

Figure 6A:
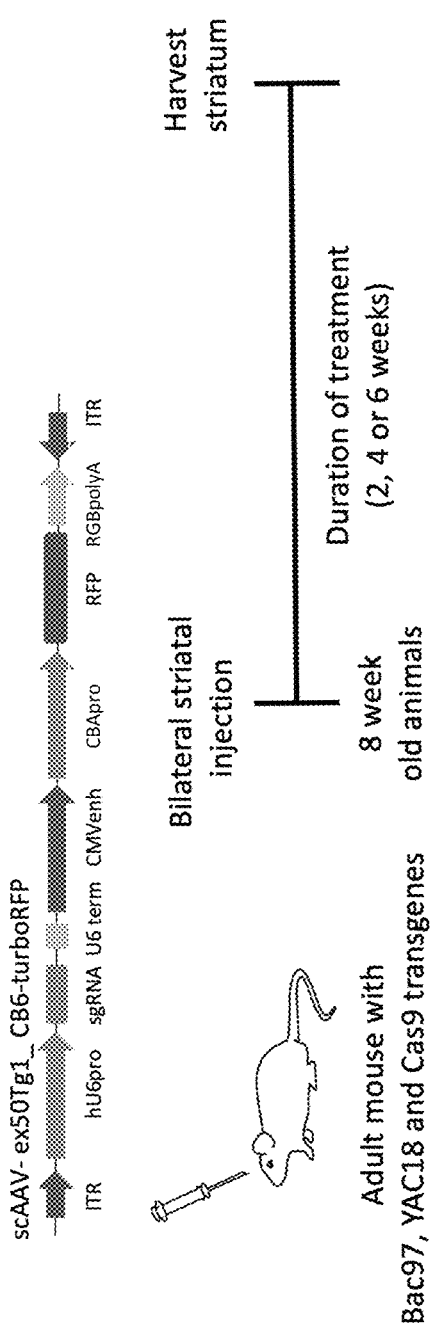
FIG. 6A-C presents exemplary data showing allele-specific CRISPR-Cas9 targeting of HTT SNPs in the adult striatum of a mouse HD model.
Figure 6C:
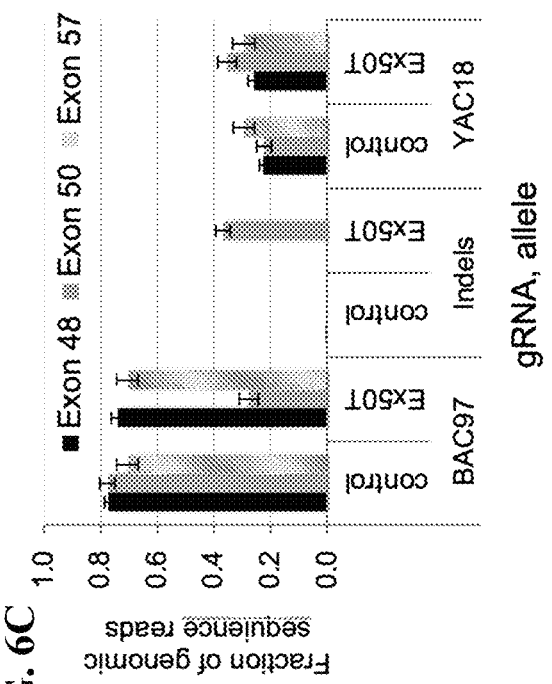
Figure 6B:
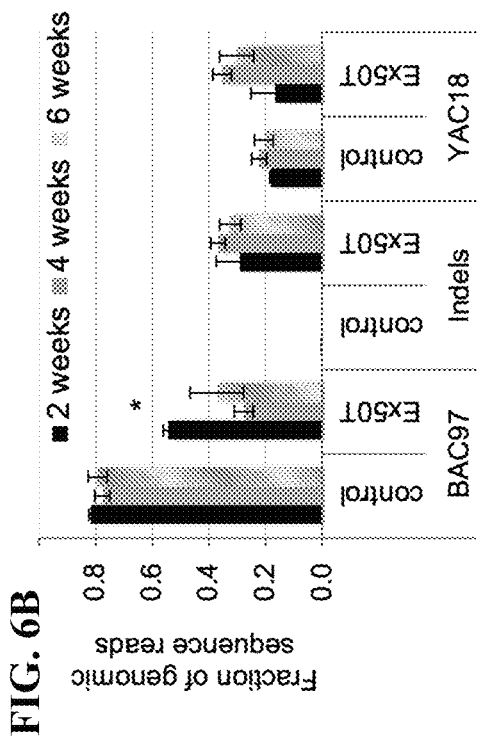

The data presented herein shows in vivo gene editing of an mHTT gene in the striatum of adult BAC97/YAC18/Cas9 mice. See, FIG. 6A-C. The Ex50Tg1 sgRNA was delivered using a scAAV9 vector that expresses the sgRNA under the control of a U6 promoter. FIG. 6A. The control was an scAAV containing an sgRNA targeting the Rosa26 locus. Vector was introduced by bilateral stereotactic injection into the adult mouse striatum. Striatal tissue samples were prepared at two, four, or six weeks following injection. A reduction in the targeted BAC97 allele was accompanied by a corresponding increase in InDel mutations. See, FIG. 6B. The induction of InDels was similar at all three time points with 37% InDels observed in the 4 weeks sample. Ninety-three percent (93%) of the InDels were frameshift mutations. Consistent with allele-specific targeting, animals transgenic for only the YAC18 transgene exhibited no InDel mutations above background following treatment (not shown). Thus, brief expression of CRISPR-Cas9 gene editing complexes in cultured neurons or extended expression in adult brain tissue induced frameshift mutations in the targeted mutant allele without altering the non-targeted normal allele.

Figure 7:
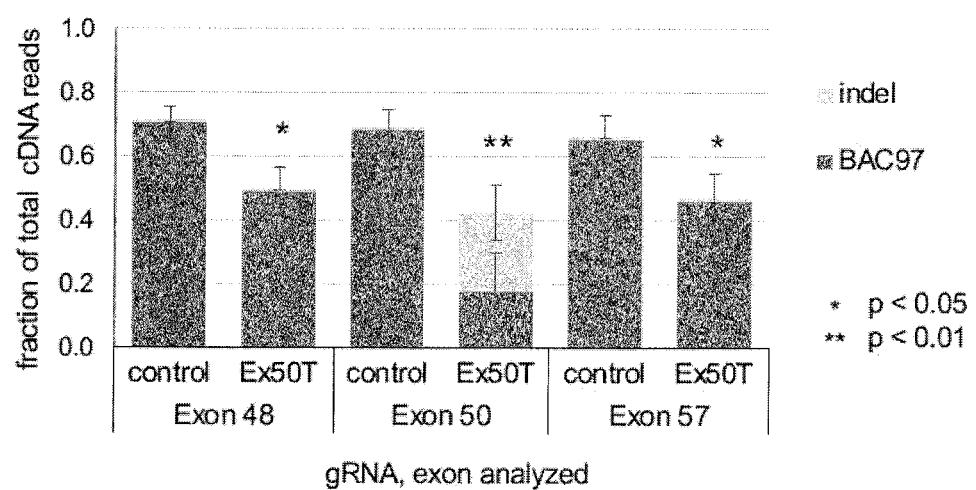
FIG. 7 presents exemplary data showing allele-specific reduction of mHTT mRNA in the mouse adult striatum. Total RNA from adult mouse striatum was reverse transcribed with gene specific primers and amplified with primers for exon 50 and two additional exons with SNP heterozygosities. Total BAC97 and InDel alleles at exon 50 in HTT RNA reveals a relative decrease in wild type BAC97 alleles and an induction of InDel alleles. The fraction of BAC97 and InDel allele reads combined is lower than the total alleles in the untreated sample. Relative levels of RNA from the targeted BAC97 transgene are also decreased at two flanking exons, even though there is no decrease in the frequency of BAC97 alleles in the corresponding genomic DNA reads (FIG. 4C). N=3 mice and error bars represent the S.E.M. p-values less than 0.05 were considered significant.

Frameshift mutations in protein coding sequences can evoke RNA surveillance mechanisms that degrade and prevent translation of mRNAs with premature termination codons. Palacios, (2013); and Popp et al, (2013). It was examined whether there was an allele-specific reduction in mHTT RNAs after inductions of mutations at exon 50. RT-PCR followed by sequencing was used to determine the relative frequencies of each HTT exon 50 SNP allele and of induced InDels in cDNA from AAV-treated striatum. At four weeks following treatment, the frequency of the targeted BAC97 mHTT allele decreased from 68% in controls to 18% when treated with Ex50T gRNA, while 25% of sequences in treated samples were induced InDel mutations. See, FIG. 7, exon 50.

Together, the frequency of all exon 50 cDNA sequences from mHTT (BAC97 sequences plus InDels) were reduced from 68% to 43%. The relative amounts of mHTT versus wild type HTT (YAC18) RNA were also assayed by sequencing heterozygous SNPs at exons 48 and 57. In genomic DNA sequences, the frequency of BAC97 alleles at exons 48 and 57 was not reduced after editing at exon 50. See, FIG. 6C. In cDNA sequences, the frequency of BAC97 alleles was significantly reduced at both flanking exons, indicating that mHTT RNA was reduced. See FIG. 7, exons 48 and 57.

Figure 8A:
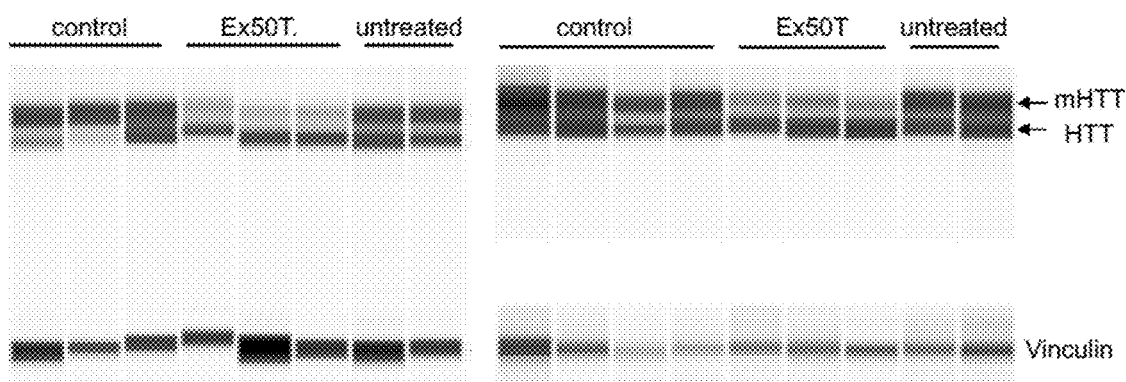
FIG. 8A-B presents exemplary data showing allele-specific reduction of mHTT protein in the mouse adult striatum. N=3 mice and error bars represent the S.E.M. p-values less than 0.05 were considered significant.
Figure 8B:
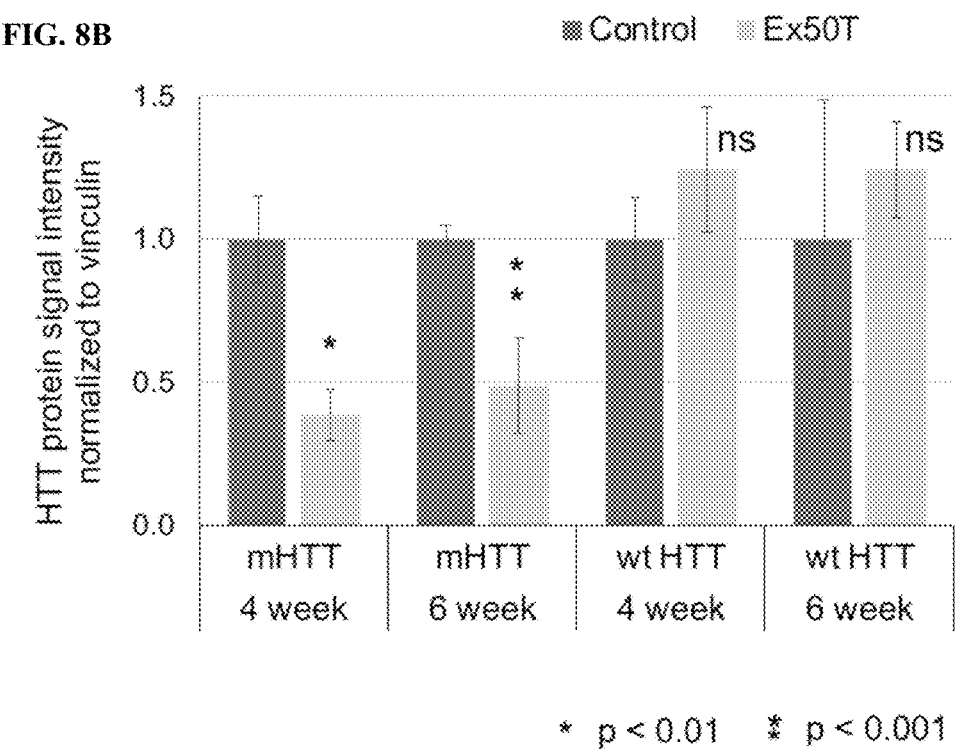
Figure 9A:
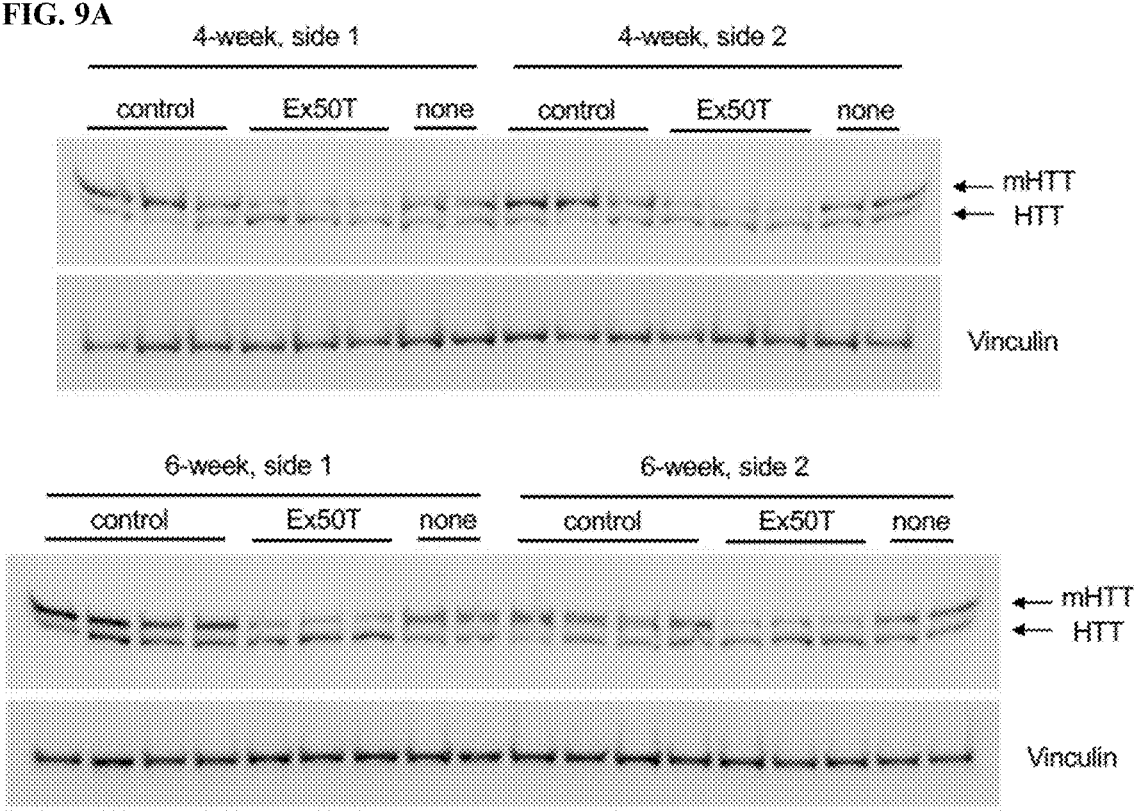
FIG. 9A-B presents exemplary data showing allele-specific reduction of mHTT protein in the adult striatum determined by Western blot.
Figure 9B:
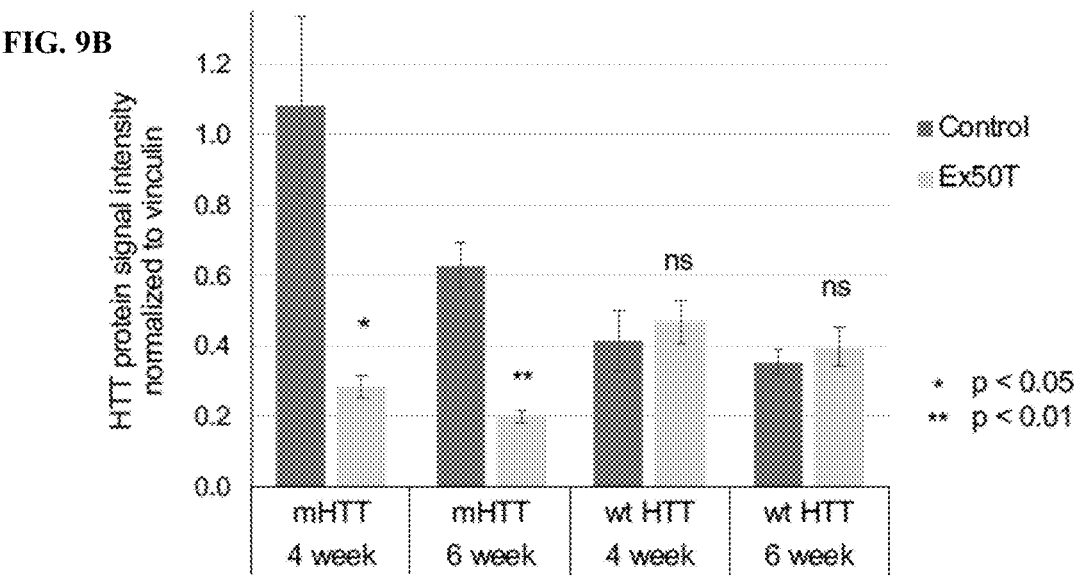

Allele-specific reduction of mHTT protein was examined at 4 and 6 weeks following sgRNA delivery to the striatum. The targeted mHTT protein (from BAC97) decreased approximately 4-fold, while wild type HTT (from YAC18) was not reduced. See, FIG. 8A-B; and FIG. 9A-B. Truncated HTT protein products were not detected in these samples. See, FIG. 10A-D. Thus, while mHTT levels were only reduced by 30%, mHTT protein levels were reduced by 75%. The previous observation that roughly half of HTT RNA is found in the nucleus of neuronal cells may partly explain this observation, since nuclear RNAs are not subject to degradation by the nonsense-mediated decay pathway. Didiot et al., (2018). Overall, these results demonstrate in vivo, allele-specific knockdown of mHTT protein in an HD mouse model in which the alleles differ by a non-tandem CAG expansion repeat SNP heterozygosity.

Figure 11A:
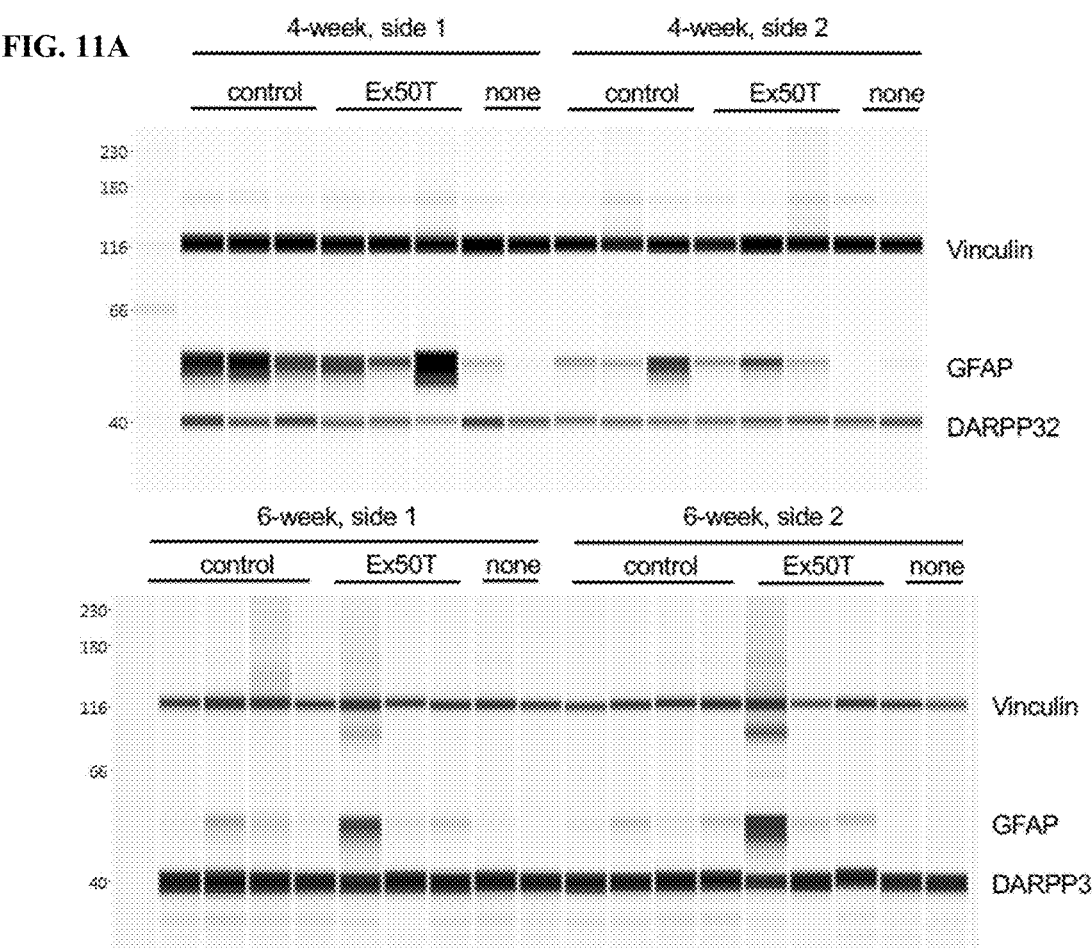
FIG. 11A-B presents exemplary data showing that markers of neuronal identity and glial cell activation are not altered in mouse striatum after scAAV9_U6gRNA injection.
Figure 11B:
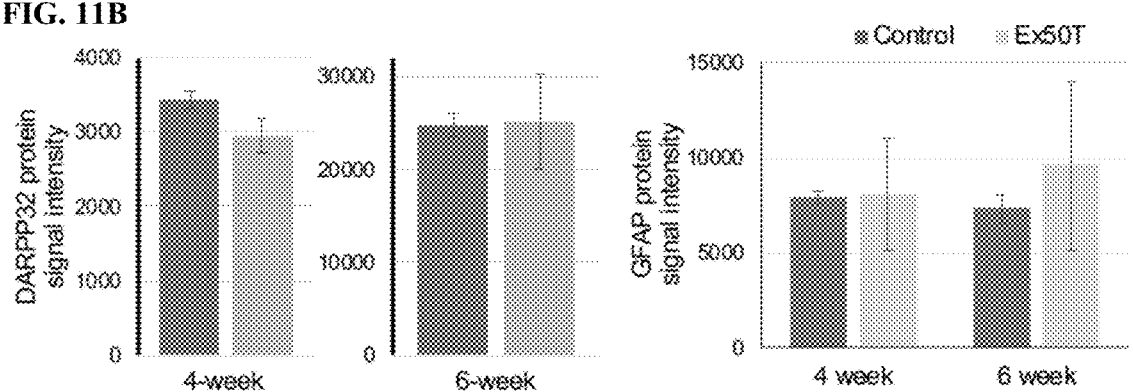
Figure 12A:
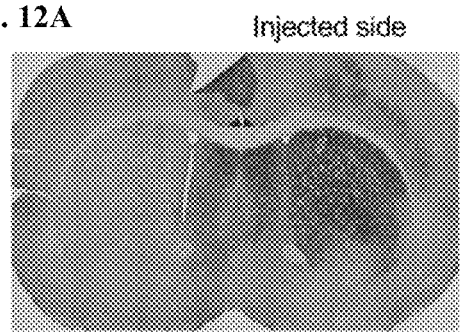
FIG. 12A-E presents exemplary data showing that markers of glial cell activation and neuronal identity are not altered in mouse striatum after scAAV9_U6gRNA injection. N=3 (mice) and error bars represent the S.E.M. p-values less than 0.05 were considered significant.
Figure 12B:
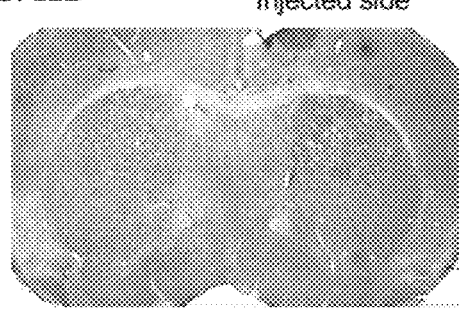
Figure 12C:
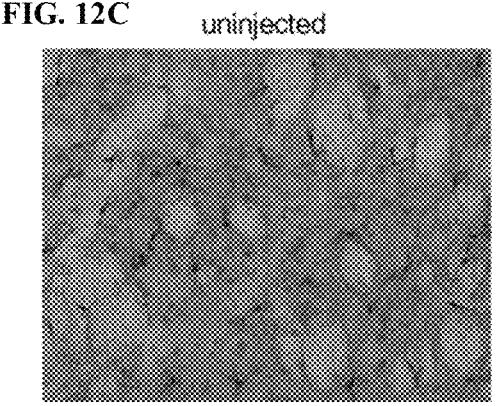
Figure 12D:
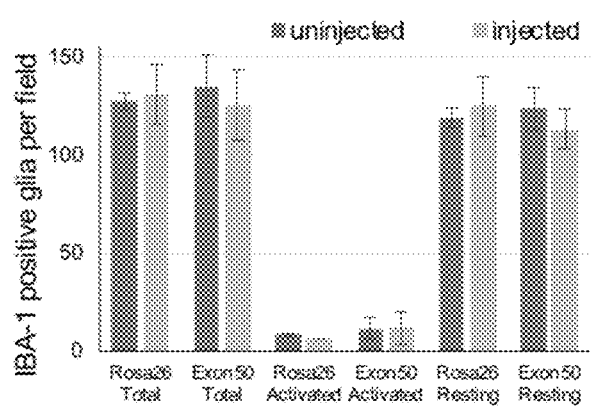
Figure 12E:
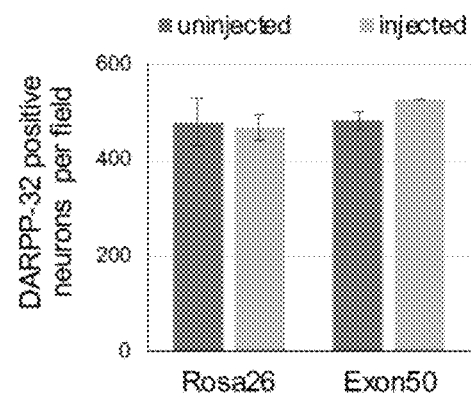

To test if either AAV delivery or CRISPR-Cas9 editing at mHTT was toxic, DARPP32 levels (which is highly enriched in striatal neurons) and GFAP levels (which is a glial stress marker) were measured. There were no changes in levels of DARPP32 or GFAP in conjunction with reduced mHTT expression. See, FIG. 11A-B. Immunohistochemical analysis of Iba1, a marker of microglia, only revealed increased staining directly adjacent to the needle injection site. See, FIG. 12C. The number of immunoreactive DARPP32 positive neurons and Iba1 positive microglia were not different between treatment groups. See, FIGS. 12D and 12E.

D. Associated Adenovirus (AAV) And Lentiviral Mediated Gene Editing

Figure 13A:
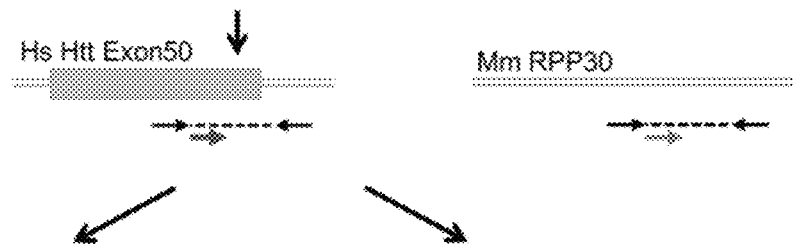
FIG. 13A-G presents exemplary data showing an analysis of non-amplified mutations by droplet digital PCR (ddPCR). N=3 (mice) and error bars represent the S.E.M. p-values less than 0.05 were considered significant.
Figure 13B:
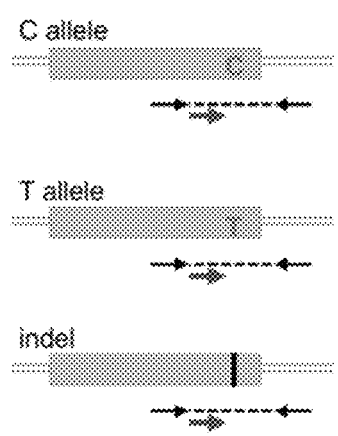
Figure 13C:
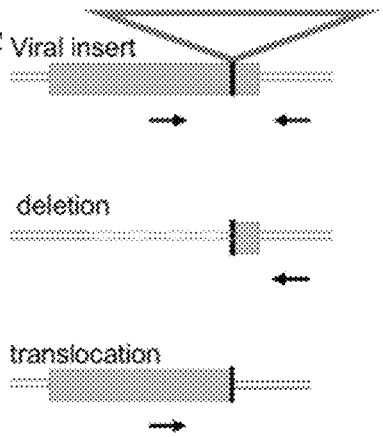

As presented above, amplicon sequencing of treated primary neurons showed an increase in the frequency of YAC18 alleles. In dividing cells, the increase might reflect gene conversion; that is, breaks in the targeted BAC97 allele could be repaired by homologous recombination using YAC18 as the donor sequence. However, homology-dependent repair is very low or absent in post-mitotic neurons. An alterative possibility is that the YAC18 allele frequency might have increased because some BAC97 alleles acquired mutations that prevent PCR amplification. These mutant alleles would not be included in the population of sequenced alleles. See, FIG. 13A-C. The fraction of exon 50 sequences that could no longer be amplified was quantified using droplet digital PCR to measure the total copy number of transgenic human exon 50. Hatch et al., (2011); and Hindson et al., (2011). A mouse reference gene (RPP30) was the diploid genome control.

Figure 13D:
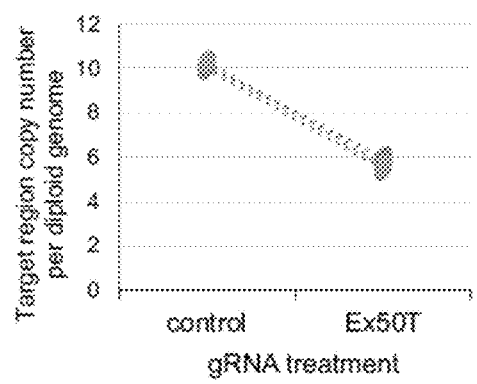
Figure 13E:
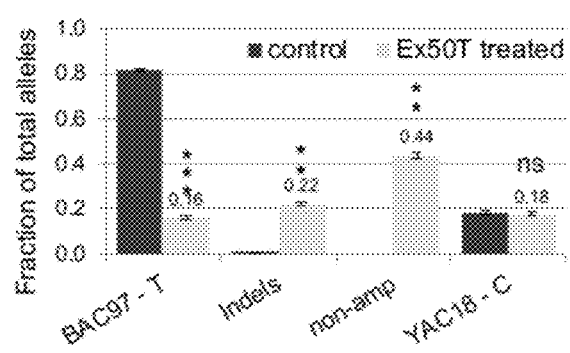
Figure 13F:
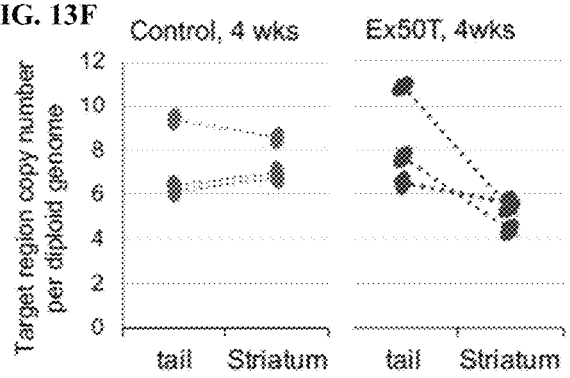
Figure 13G:
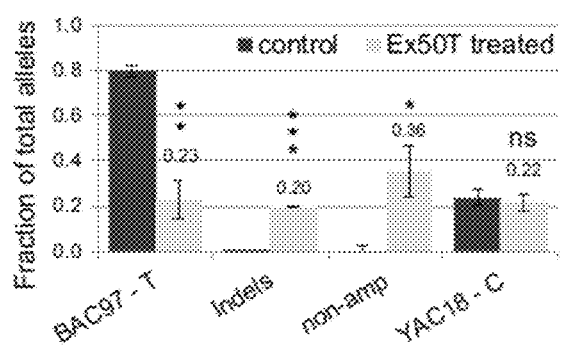

Paired samples were obtained by treating primary neurons derived from individual animals with either control or Ex50T gRNAs. The measured human HTT exon 50 copy number was decreased by an average of 44% in Ex50T-treated versus control cells. See, FIG. 13D. The estimated fraction of non-amplifiable alleles was added to the sequenced alleles shown in FIG. 3B to infer the actual fraction of each allele class. See, FIG. 13E. The inferred frequency of unaltered BAC97 alleles was 16% in Ex50T treated samples after including 44% non-amplified alleles in treated samples. The inferred frequency of induced InDel mutations was 22%. Together, the frequency of non-amplified alleles plus InDel mutations represented 66% of alleles in the treated sample. In this analysis, the non-targeted YAC18 alleles were unchanged by editing, remaining at 18%. Editing in the striatum generated a similar result. See, FIGS. 13F and 13G. Thus, in both primary neurons and striatum, AAV delivery of sgRNAs induced a combination of InDel mutations, which were included in the presently disclosed sequenced alleles, and an additional class of mutations that were not represented in the sequenced amplicons. The relative frequency of each of these classes can be inferred by ddPCR quantification of the missing alleles.

One possible class of non-amplifiable alleles are large deletions flanking the editing site. To determine if very large deletions were removing the BAC97 allele at exon 50, the frequency of SNP heterozygosities was examined at flanking exons 48 and 57. There was no significant change in the BAC97 or YAC18 allele at either flanking SNP site. See, FIG. 6C. These data indicate that the mutations that prevent amplification were not deletions spanning these additional SNPs.

Figure 14A:
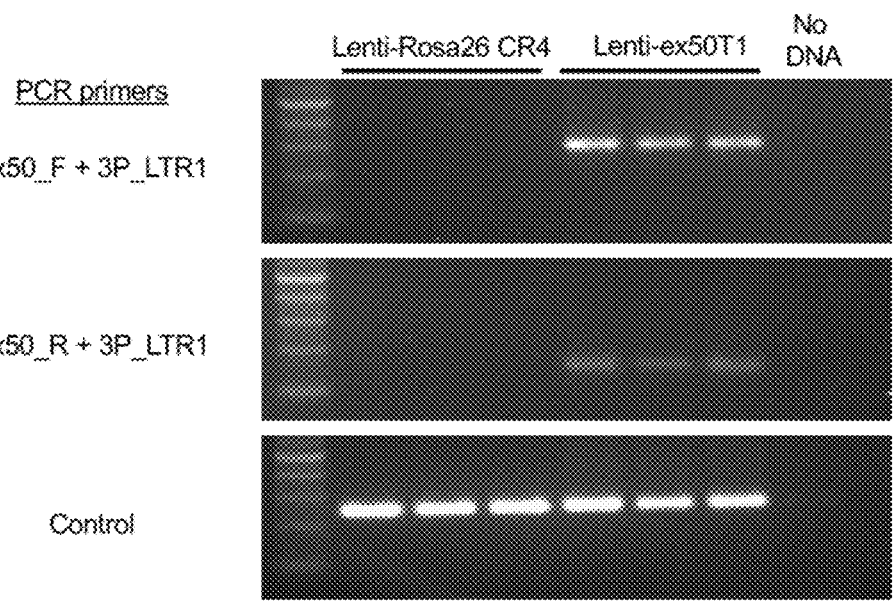
FIG. 14A-B presents exemplary data demonstrating Cas9 nuclease-induced insertion of lentivirus and AAV vectors.
Figure 14B:
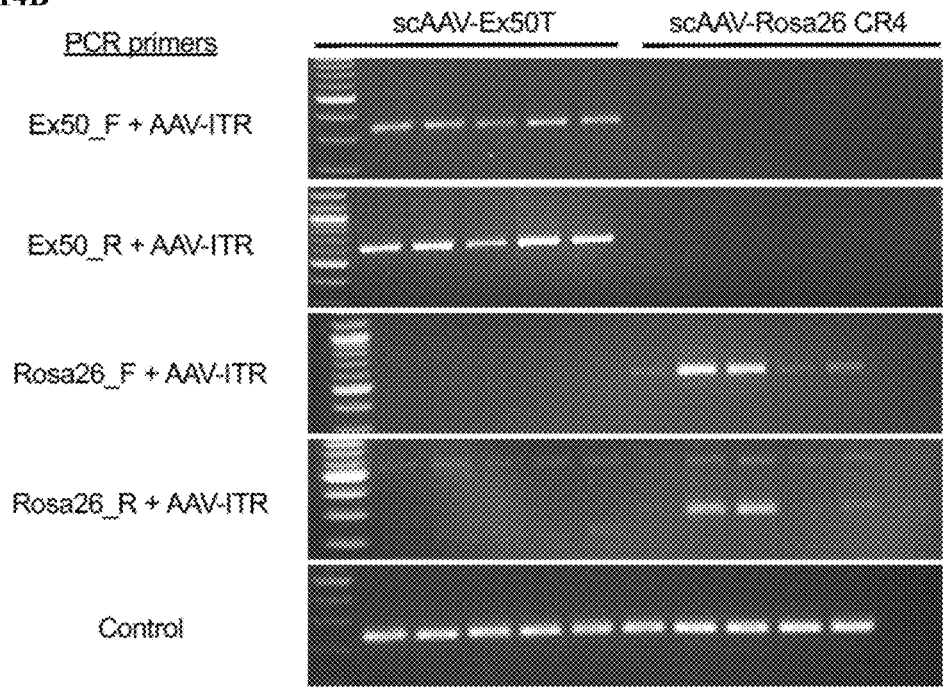

Previous studies reported that AAV-mediated delivery of CRISPR-Cas9 generated a high rate of AAV insertions in various mouse tissues, including normal mouse brain. Hanlon et al., (2019); Nelson et al., (2019). To determine if viral insertions at the editing site contributed to the non-amplifiable alleles, PCR was used to detect lentiviral and AAV insertions. Insertions were detected human HTT exon 50 locus or the control Rosa26 locus following treatment with gRNAs targeting each genomic site. See, FIG. 14A-B. Insertions were only detected at the site targeted by the corresponding gRNA, demonstrating that delivery of gene editing components by lentiviral or AAV induces viral insertion mutations at the editing target site. This is believed to be the first demonstration that integration-competent lentivirus, which typically integrates at random genomic sites, was directed to integrate at DNA breaks induced by CRISPR-Cas9 gene editing.

E. Allele-Specific Gene Editing in HD Patient-Derived Fibroblasts

The data presented herein show that primary and adult mouse neurons with the BAC97 and YAC18 transgenes provide a model system to study DNA repair and HTT gene expression in post-mitotic neurons. Human fibroblasts heterozygous for the common HTT coding region SNPs were used to examine the effect of SNP targeting in human cells with single copy HTT genes. Unlike post-mitotic neurons, fibroblasts can carry out homology dependent repair, using the non-targeted allele to repair the targeted SNP, resulting in an increase in the non-targeted allele.

Insertion and deletion (InDel) allele frequencies were determined using the CRISPResso software package. In Ex50Tg1 treated cells, a subset of deletions span the SNP site and cannot be assigned to one of the starting alleles; however, all of the remaining InDel mutations shown are associated with the targeted allele. In Ex48Gg2 treated cells, the most frequent InDel alleles are all associated with the targeted allele.

Figure 15:
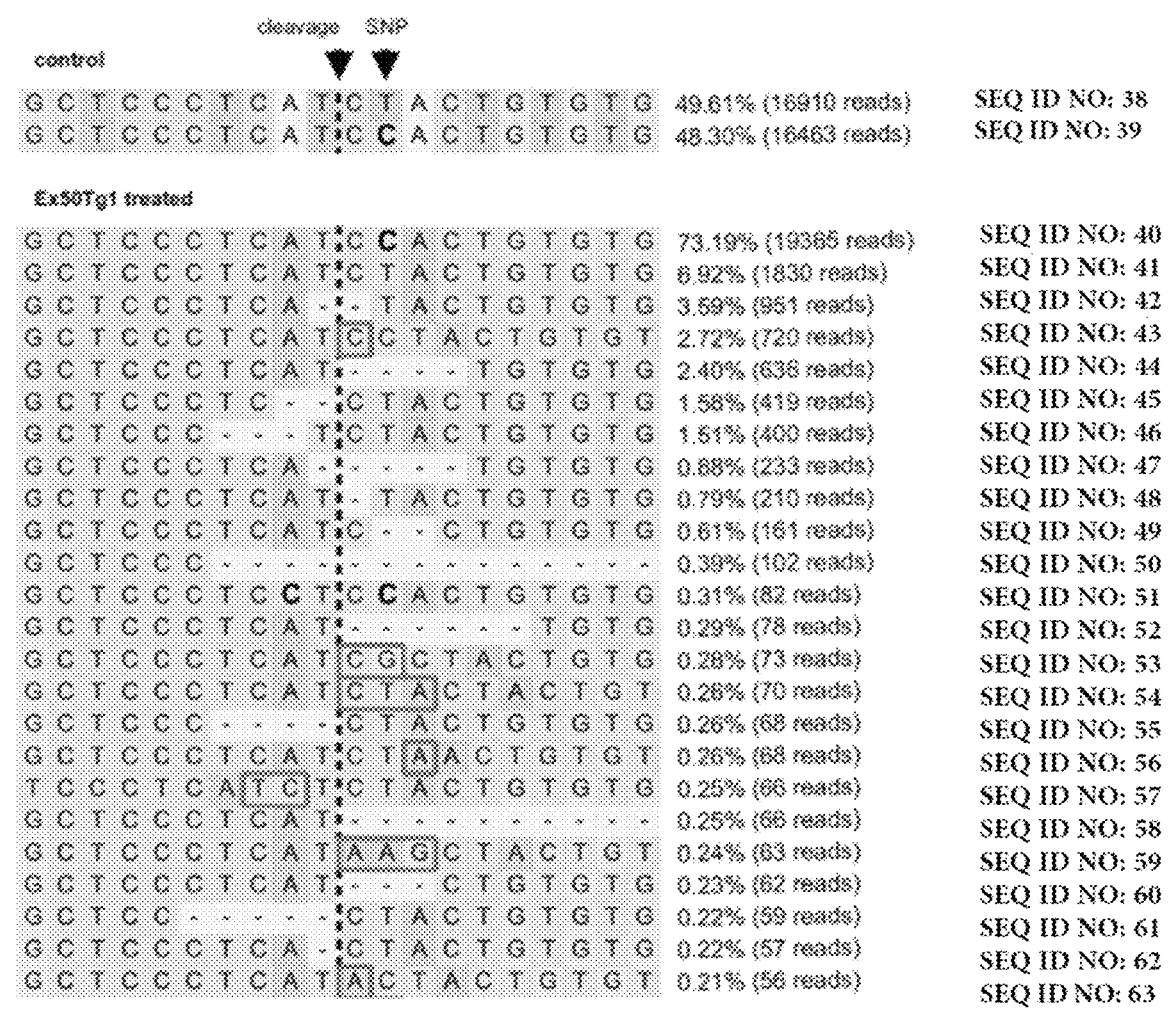

The data show that untreated fibroblasts had an equal frequency of each allele. Treated fibroblasts exhibited an induction of InDels (19%), a reduction of the targeted allele (50 to 7%), and a large increase in the non-targeted allele (50 to 74%). Sequencing of the individual alleles revealed that most or all InDels were derived from the targeted allele. See, FIG. 15. These results confirm that the allele-specificity observed in transgenic HD mouse models is observed in HD patient derived cell types.

EXPERIMENTAL

Example I

Experimental Models and Subjects
Mice

All mice used in this study were housed in the University of Massachusetts vivarium on a 12/12 light cycle with free access to food and water. All animal protocols were approved in the University of Massachusetts Medical School's IACUC protocol #A978-18.

The BAC97 transgenic mice (FVB/N-Tg (HTT*97Q) LXwy/ChdiJ) were obtained from William Yang at UCLA. Gray et al., (2008). BAC97 mice express a neuropathogenic, full-length human mutant Huntingtin gene modified to harbor a loxP-flanked human mutant htt exon 1 sequence containing 97 mixed CAA-CAG repeats.

YAC18 transgenic mice (FVB/N-Tg (HTT*18Q) were obtained from Michael Hayden at the University of British Columbia. Hodgson et al., (1999). YAC18 mice have a normal length human Huntingtin (18 polyglutamate repeats).

YAC18 or BAC7, Hdh−/+ animals were obtained by crossing the YAC18 and BAC97 mice with Hdh−/+ (Huntingtin null) mice obtained from William Yang. Zeitlin et al., (1995). A second cross produced YAC18 BAC97 mice with no endogenous mouse Huntington (YAC18 BAC97 Hdh−/−). Repeat lengths were checked by PCR and sequencing to ensure that there was no genetic drift. Cas9 knock in mice (Cas9: Gt (ROSA) 26Sor/J) were obtained from Jackson labs and were crossed with BAC97 mice to produce BAC97 mice homozygous for Cas9. Platt et al., (2014).

To generate YAC18 BAC97 mice with Cas9, BAC97 Cas9 homozygous mice were crossed with YAC18 mice (YAC18 BAC97 Hdh-/- Cas9 het).

Cell Lines

Human HD fibroblast line GM02173 was obtained from Coriell Institute for Medical Research. Fibroblasts were cultured in MEM +15% FBS, 1% Pen/Strep, 1% Non-Essential Amino Acids, 1% Essential Amino Acids and 2% Vitamins with the pH adjusted to 7.4 (prepared by UMASS Tissue Culture Core).

HEK293T cells were obtained from Dr. Michael Green (UMass Medical School) and cultured in high glucose DMEM (Invitrogen, 11965118) containing 10% FBS (Atlanta Biologicals premium select) and 1% pen/strep (Invitrogen, 15140122). Cells were grown at 37 C with 5% CO2.

Primary Cell Cultures

Primary cortical neurons were isolated from YAC18 BAC97 Hdh-/- Cas9 E16.5 embryos. Brains were removed and placed in cold Hibernate E media (Brain bits LLC, HE) and the cortex was quickly dissected and incubated at 37° C. for 45 minutes in papain dissolved in Hibernate E plus DNAse (Brain Bits, LLC). Cells were dissociated by triturating in Neural Q media (Sigma-Aldrich) containing GS21 (Sigma-Aldrich, G0800) plus 2.5% heat inactivated FBS (Gibco). Cells were plated in 6-well Poly L Lysine coated plates at 1 million cells per well and incubated at 37 C with 5% CO2. Cells were fed every 48 hours.

Example II

Guide RNA Design

Target sites for the CRISPR-SpCas9 nuclease were designed using the opensource Bioconductor software package CRISPRseek. Zhu et al., (2014). CRISPR-Cas9 target sites were selected in which a SNP heterozygosity is expected to affect target recognition because the polymorphic position was in the PAM sequence or close to the nuclease cleavage site. A list of Htt-specific sgRNAs are listed in Table 1.

Example III

In Vitro Validation of Guide RNAs

The Htt specific sgRNA sequences listed in Table 1 were cloned into the BbsI site of the pX330 vector (Addgene 42230) using overlapping oligonucleotides and T4 DNA polymerase (New England BioLabs, M02030L). Cong et al., (2013)

Overlapping oligonucleotides containing the sgRNA sequence and 19 bases of complementary sequence to the overhangs generated by a BbsI digest of the pX330 vector were designed. Forward and reverse oligonucleotides were annealed and then cloned directly into the pX330 vector digested with BbsI restriction enzyme. The final pX330 constructs were verified by Sanger sequencing (Macrogen, USA). Target sequences for in vitro validation of the sgRNAs were cloned similarly into the SbfI site of the pM427 GFP reporter vector (Wilson et al., 2013).

For cloning into the pM427 vector, oligonucleotides were designed with the target sequence for the appropriate sgRNA and 19 bp of complementary sequence to the SbfI generated overhangs. The final reporter constructs were verified by Sanger sequencing (Macrogen, USA). To test the efficiency of the sgRNAs to cut their target sequence, HEK293T, cells were co-transfected with 150 ng of the pM427 GFP reporter plasmid containing sgRNA target sequences, 50 ng of the specific pX330 sgRNA plasmid, 50 ng Cas9 expressing plasmid, and 100 ng of a mCherry plasmid (to monitor transfection efficiency) using Polyfect transfection reagent (Qiagen, 301105). Percent GFP expressing cells (positive events) were determined 48 hours post transfection by flow cytometry (Becton Dickinson FACScan). Experiments were performed in triplicate and data is reported as the mean+/-S.E.M.

Example IV

Lentivirus Infections

Htt Ex50Tg1 and Rosa26 sgRNAs were cloned into lentiCRISPRv2GFP plasmid (Addgene, 82416) that was modified to include a CMV promoter to enhance GFP expression. Walter et al., (2017). The sgRNAs were cloned into the BsmbI sites using annealed oligonucleotides containing appropriate ligation adaptors and T4 polymerase (New England BioLabs, M02030L).

Ex50Tg1_LentiCRISPRv2_CMVGFP and Rosa26CR4_LentiCRISPRv2 CMVGFP plasmids were confirmed by Sanger sequencing (Macrogen USA) and restriction digests. High titer Lentivirus was produced as described. Sena-Esteves et al., (2004). Approximately $20 \times 10^6$ HEK 293T cells were transfected with 18 μg of LentiCRISPR plasmid with sgRNA sequence, 18 μg of cmvdR8.91, and 12 μg vsv-g using calcium chloride. Viral supernatant was collected, filtered sterilized using a Durapore PVDF filter, concentrated by ultracentrifugation and resuspended in Opti-MEM reduced serum media (ThermoFisher, 31985070). TU/ml were determined by serial dilution and ImageJ analysis of GFP positive cells. For infection of human HD fibroblasts (Coriell Institute for Medical Research GM02173), were plated at a density of 100,000 cells per well in a 6-well plate. One day after plating 0.5 ml of media containing polybrene (16 μg/ml) and Ex50Tg1 or Rosa26 lentivirus (MOI 50) was added to wells.

Cells were incubated overnight and fresh media was added the following day. Cells were collected 7 days after infection for analysis. For infection of YAC18 BAC97 Hdh$^{-/-}$ Cas9 mouse primary neurons, 40 μl of the Ex50Tg1 and Rosa26 lentivirus ($1 \times 10^8$ TU/ml) was added (no polybrene) five days after plating. Primary neurons were fed every 48 hours and harvested 7 days after infection.

Genomic DNA was prepared from cell pellets using the DNeasy Blood and Tissue kit (Qiagen, 69506) according to the manufacturers protocol. Following DNA extraction, genotypes were verified, sgRNAs, and the editing efficiency for each infection by PCR and Sanger sequencing. Experiments were performed in triplicate and data is reported as the mean+/-SEM.

Example V

AAV Injections

Htt Ex50Tg1 and Rosa26 sgRNAs were cloned into the scAAV_CB6_TurboRFP_RBG vector. U6 promoter plus guide was amplified from the appropriate pX330 construct and cloned into the SalI site using T4 polymerase (New England BioLabs, M02030L). Ex50Tg1_scAAV_CB6_TurboRFP_RBG and Rosa26CR4_scAAV_CB6_TurboRFP_RBG constructs were confirmed by Sanger sequencing (Macrogen USA) and restriction digests.

AAV vectors were packaged into the AAV-AS serotype (Choudhury et al., 2016). Subsequently, direct injection of the AAV vectors into the mouse striatum was performed by the UMASS Viral Vector Core. For injection of AAV, eight weeks old, age matched YAC18 BAC97 Hdh-/- Cas9 mice were anesthetized with 284 mg/kg tribromoethanol and placed in a stereotactic apparatus. The fur was removed from the injection area and the skin was cleaned with betadine followed by 70% alcohol. An incision was made to expose the skull and a 33 ga needle was guided by stereotaxis and positioned over the bregma. The injection coordinates were measured from the bregma (1.0 mm anterior, 2.0 mm lateral and 3.0 mm from the surface of the brain) and a small hole was made with a micro drill. The needle was lowered into position and 3 µl of experimental virus ($3.4 \times 10^9$) or control virus was injected at 0.125 µl/min using an UltraMicroPumpII (World Precision Instruments). Following the injection, the incision was closed using 5-0 Vicryl Rapid suture (Ethicon). Mice were monitored following surgery and were returned to the mouse room when they were awake and moving in the cage. They received Ketofen 5 mg/kg to alleviate post-surgical pain.

Mice were sacrificed at either two, four, or six weeks post injection using tribromoethanol followed by cervical dislocation. Brains were quickly removed and placed in cold artificial CSF. They were immediately sliced in cold artificial CSF using a VT1000s vibratome set for 300 microgram slices. The striatal tissue was collected using a 2 mm biopsy punch and slices for protein were immediately frozen on dry ice. Slices for RNA and DNA analysis were placed in RNAlater (Sigma-Aldrich R0901) overnight and then stored at −80° C. until processing. DNA and RNA was prepped using the Allprep DNA/RNA/Protein Mini Kit (Qiagen, 80004) according to the manufacturers protocol. Genotypes and virus were confirmed by PCR and Sanger sequencing. Initial editing efficiencies were assessed by PCR and Sanger sequencing.

Example VI

DNA/RNA Extraction and Illumina Sequencing

DNA was prepared using either the DNEasy Blood and Tissue Kit (Qiagen, 69506) or the Allprep DNA/RNA/Protein Mini Kit (Qiagen, 80004) according to the manufacturers protocol. Genotypes and virus were confirmed by PCR and Sanger sequencing.

Initial editing efficiencies were assessed by PCR and Sanger sequencing. RNA for RNA-seq was prepared using the Qiagen AllPrep DNA/RNA/Protein Mini Kit (Qiagen, 80004). From each total RNA sample cDNA was generated using the Qiagen OneStep RT-PCR kit (Qiagen, 210210). Gene specific primers with overhangs that are complementary to TruSeq barcode primers were designed to amplify approximately 150 bp target sequences.

Fifty (50) ng of genomic DNA was PCR amplified using Phusion High Fidelity DNA Polymerase (New England Biolabs, M0530L) (98° C. 10s, 65° C. 15s, 72° C. 30s for 30 cycles). PCR fragments were gel extracted using QIAquick Gel Extraction kit (Qiagen) and quantified by nanodrop or gel electrophoresis. 2 ng of the target amplicon was then PCR amplified using i5 and i7 TruSeq primers containing unique barcodes: 98° C. 30s 61° C. 25s 72° C. 17s for 9 cycles.

Barcoded products were quantified using ImageJ and equal amounts of amplicons were pooled. The pooled library was purified by gel extraction (Qiagen, 28706), concentrated (Zymo DNA Clean and Concentrator Kit, D4013), and quantified by gel electrophoresis and nanodrop. Barcoding efficiency was determined by cloning (CloneJET PCR Cloning Kit, ThermoFisher, K1232) and Sanger sequencing. 200 ng of the library was submitted to the UMASS Medical School Deep Sequencing Core for paired-end sequencing.

Example VII

CRISPResso/SNP Classifier Software

FastQ files were processed using the CRISPResso software package to quantify the frequency of each unmodified SNP allele and the frequency, size and position of induced insertion/deletion (indel) mutation. Pinello et al., (2016). A custom python code was used to assign indel mutations to a parental SNP allele.

Insertion and deletion mutation sequences were extracted from the allele frequency table generated by CRISPResso. Sequence similarity scores to each parental allele were obtained by BLAST. Altschul et al., (1990). The mutation was assigned to the allele with greater similarity. When the scores were identical (e.g. when a deletion includes the SNP base position), the parental allele was designated as "not determined".

Example VIII

TIDE Analysis

Chromatograms generated by PCR sequencing were analyzed with the TIDE web tool (tide.deskgen.com). The guide RNA sequence used in the analyses was CATCTACTGTGTGCACTTCA (SEQ ID NO: 13). Both "forward" and "reverse" reads were assayed and the reverse complement of the guide RNA was used for the reverse reads. The decomposition window was limited to 100 bases; otherwise, default parameters were applied. For each chromatogram, the total efficiency percent and the R2 values were recorded.

Example IX

Protein Analysis

Frozen tissue punches from one striatal hemisphere were homogenized in 10 mM HEPES pH7.2, 250 mM sucrose, 1 mM EDTA plus protease inhibitors (Roche, 11836170001), 1 mM NaF, 1 mM $Na_3 VO_4$ on ice. Lysates were then sonicated for 10 seconds and protein concentration was determined using the Bradford method (BioRad, 5000006).

HTT levels were characterized using a Simple Western assay (Wes, ProteinSimple). Equal concentrations of lysates (0.2 mg/ml) were used with a 66-440 kDa capillary cartridge (Protein Simple, SM-W008). Primary antibodies were anti-HTT Ab1 (aa1-17, 1:50, DiFiglia, M et al. Neuron 1995, 14:1075-1081) and anti-vinculin (1:2000, Sigma V9131). The manufacturer's recommended protocol was followed and analysis was performed using Compass software (ProteinSimple). HTT peak areas were determined using dropped peak setting and normalized to vinculin peak areas.

Western blots on the same lysates were performed as previously described (Keeler, A M et al. JHD 2016, 5:239-248). Briefly, 10 mg lysates were separated by SDS-PAGE using 3-8% Tris acetate gels (Life Technologies, EA03785BOX) or 4-12% Bis-Tris gels (Life Technologies, NP0336BOX) and transferred to nitrocellulose using Trans-Blot Turbo apparatus (BioRad, 1704150). Blots were then blocked in 5% milk/TBS+0.1% Tween 20, incubated in primary antibody diluted in blocking buffer overnight at 4 C, then secondary antibody diluted in blocking buffer 1 hour at RT. Blots were washed and signal was detected using Super Signal West Pico Plus Chemiluminescent kit (Pierce, 34580)

and a CCD imaging system (Alpha Innotech) or Hyperfilm ECL (GE Healthcare, 28906839).

Bands were manually circled and area and mean gray value were measured using ImageJ software (NIH). Total signal intensity for each band was determined by multiplying area by mean gray value.

Primary antibodies were rabbit polyclonal anti-HTT antibody Ab1 (1:2000), mouse monoclonal anti-polyglutamine antibody 1C2 (1:6000, Millipore, MAB1574), mouse monoclonal anti-b-tubulin (1:6000, Sigma, T8328), rabbit polyclonal anti-GFAP (1:8000, Millipore, AB5804), rabbit monoclonal anti-DARPP32 (1:10,000, Abcam, AB40801) and rabbit polyclonal anti-Iba1 (1:500, Wako, 019-19741). Secondary antibodies were peroxidase-labeled anti-rabbit IgG (1:2500, Jackson Immunoresearch, 711035152) or anti-mouse IgG (1:5000, Jackson Immunoresearch, 715035150).

Example X

Conventional and Droplet Digital PCR to Detect Viral Insertions

For conventional PCR approximately 100 ng of template genomic DNA was amplified with Phusion High Fidelity polymerase (New England Biolabs, M0530L) using the following conditions: 98° C. for 1.5 min, 30 cycles at 98° C. for 10s, 65° C. for 15s, 72° C. for 30s and a final extension at 72° C. for 10 min.

PCR products were analyzed on a 2% agarose gel and imaged on a UVP Epi Chemi II Darkroom Bioimaging system (Analytikjena). Droplet digital PCR reactions were performed using Droplet Digital PCR Supermix for Probes (no dUTP) (BioRad, 186-3023) according to the manufacturer's instructions. Briefly 50 ng of template genomic DNA was amplified using the following thermal cycling conditions: enzyme activation 95° C. for 10 min, followed by 40 cycles of 94° C. 30s, 60° C. 1 min, and a final enzyme deactivation step at 98° C. for 10 min. Droplets were generated and analyzed with the QX200 Droplet Digital PCR System (BioRad).

Example XI

Immunohistochemistry for DARP32 and IBA1

Mice were anesthetized with an overdose of tribromoethanol and perfused with 15 mL of phosphate buffered saline (PBS), followed by 30 mL of 4% paraformaldehyde. Brains were removed and post-fixed in 2% paraformaldehyde overnight at 4° C. and stored in PBS until processing. Brains were sliced (40 micrometers) on the Vibratome s1000 (Leica Biosystems) through the striatum. Every fifth section was used for immunohistochemistry staining. Sections were stained with an anti DARP rabbit monoclonal antibody (1:50,000 dilution) or anti-IBA1 (Wako, 01919741, 1:1,000 dilution) overnight at 4° C. Secondary antibody (anti-Rabbit ImmPRESS Kit, Vector Labs, MP-7801; not diluted) was applied for 30 minutes. Metal Enhanced DAB kit (ThermoFisher Scientific, 34065) was used to visualize positive cells.

Quantification was done by taking images (20× for DARP32 and 40× for IBA1) with a Nikon Eclipse E600 microscope and a Nikon-Qi1MC camera with NIS-Elements. To capture images consistently between multiple brain sections, the first image was taken in the center of the striatum and the stage was move 0.5 mm toward the dorsal edge. After the second image was taken, the stage was moved back 0.5 mm to the original position and then 0.5 mm further toward the ventral edge. After the third image was taken, the stage was moved 0.5 mm back to the original position. Two more images were taken by moving the stage 0.5 mm to the right of the center and 0.5 mm to the left of the center. A total of 10 pictures were taken per tissue section and there were five total sections analyzed per animal (every 10th section through the striatum). Random numbers were assigned to each image to eliminate any bias during cell quantification. The cells were counted using ImageJ software.

Example XII

Quantification and Statistical Analysis

Linear regression was used to quantify and test the statistical significance between treatment conditions within genotype or treatment duration and between genotype or treatment duration within treatment groups. Analyses were conducted using STATA (v16) software's regression command to fit models for each dependent variable then using post-estimation contrasts to test each hypothesis. p-values less than 0.05 were considered to be statistically significant.

REFERENCES

Alterman, J. F., Godinho, B., Hassler, M. R., Ferguson, C. M., Echeverria, D., Sapp, E., Haraszti, R. A., Coles, A. H., Conroy, F., Miller, R., et al. (2019). A divalent siRNA chemical scaffold for potent and sustained modulation of gene expression throughout the central nervous system. Nat Biotechnol 37, 884-894.

Aronin, N., Chase, K., Young, C., Sapp, E., Schwarz, C., Matta, N., Kornreich, R., Landwehrmeyer, B., Bird, E., Beal, M. F., et al. (1995). CAG expansion affects the expression of mutant Huntingtin in the Huntington's disease brain. Neuron 15, 1193-1201.

Burrus, C. J., Mckinstry, S. U., Kim, N., Ozlu, M. I., Santoki, A. V., Fang, F. Y., Ma, A., Karadeniz, Y. B., Worthington, A. K., Dragatsis, I., et al. (2020). Striatal Projection Neurons Require Huntingtin for Synaptic Connectivity and Survival. Cell Rep 30, 642-657 e646.

Chao, M. J., Gillis, T., Atwal, R. S., Mysore, J. S., Arjomand, J., Harold, D., Holmans, P., Jones, L., Orth, M., Myers, R. H., et al. (2017). Haplotype-based stratification of Huntington's disease. Eur J Hum Genet 25, 1202-1209.

Choudhury, S. R., Harris, A. F., Cabral, D. J., Keeler, A. M., Sapp, E., Ferreira, J. S., Gray-Edwards, H. L., Johnson, J. A., Johnson, A. K., Su, Q., et al. (2016). Widespread Central Nervous System Gene Transfer and Silencing After Systemic Delivery of Novel AAV-AS Vector. Mol Ther 24, 726-735.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Didiot, M. C., Ferguson, C. M., Ly, S., Coles, A. H., Smith, A. O., Bicknell, A. A., Hall, L. M., Sapp, E., Echeverria, D., Pai, A. A., et al. (2018). Nuclear Localization of Huntingtin mRNA Is Specific to Cells of Neuronal Origin. Cell Rep 24, 2553-2560 e2555.

DiFiglia, M., Sapp, E., Chase, K., Schwarz, C., Meloni, A., Young, C., Martin, E., Vonsattel, J. P., Carraway, R., Reeves, S. A., et al. (1995). Huntingtin is a cytoplasmic protein associated with vesicles in human and rat brain neurons. Neuron 14, 1075-1081.

Dragatsis, I., Levine, M. S., and Zeitlin, S. (2000). Inactivation of Hdh in the brain and testis results in progressive neurodegeneration and sterility in mice. Nat Genet 26, 300-306.

Evers, M. M., Miniarikova, J., Juhas, S., Valles, A., Bohuslavova, B., Juhasova, J., Skalnikova, H. K., Vodicka, P., Valekova, I., Brouwers, C., et al. (2018). AAV5-miHTT Gene Therapy Demonstrates Broad Distribution and Strong Human Mutant Huntingtin Lowering in a Huntington's Disease Minipig Model. Mol Ther 26, 2163-2177.

Garriga-Canut, M., Agustin-Pavon, C., Herrmann, F., Sanchez, A., Dierssen, M., Fillat, C., and Isalan, M. (2012). Synthetic zinc finger repressors reduce mutant huntingtin expression in the brain of R6/2 mice. Proc Natl Acad Sci USA 109, E3136-3145.

Gray, M., Shirasaki, D. I., Cepeda, C., Andre, V. M., Wilburn, B., Lu, X. H., Tao, J., Yamazaki, I., Li, S. H., Sun, Y. E., et al. (2008). Full-length human mutant huntingtin with a stable polyglutamine repeat can elicit progressive and selective neuropathogenesis in BACHD mice. J Neurosci 28, 6182-6195.

Hanlon, K. S., Kleinstiver, B. P., Garcia, S. P., Zaborowski, M. P., Volak, A., Spirig, S. E., Muller, A., Sousa, A. A., Tsai, S. Q., Bengtsson, N. E., et al. (2019). High levels of AAV vector integration into CRISPR-induced DNA breaks. Nat Commun 10, 4439.

Harper, S. Q., Staber, P. D., He, X., Eliason, S. L., Martins, I. H., Mao, Q., Yang, L., Kotin, R. M., Paulson, H. L., and Davidson, B. L. (2005). RNA interference improves motor and neuropathological abnormalities in a Huntington's disease mouse model. Proc Natl Acad Sci USA 102, 5820-5825.

Hatch, A. C., Fisher, J. S., Tovar, A. R., Hsieh, A. T., Lin, R., Pentoney, S. L., Yang, D. L., and Lee, A. P. (2011). 1-Million droplet array with wide-field fluorescence imaging for digital PCR. Lab Chip 11, 3838-3845.

Heidenreich, M., and Zhang, F. (2016). Applications of CRISPR-Cas systems in neuroscience. Nat Rev Neurosci 17, 36-44.

Hindson, B. J., Ness, K. D., Masquelier, D. A., Belgrader, P., Heredia, N. J., Makarewicz, A. J., Bright, I. J., Lucero, M. Y., Hiddessen, A. L., Legler, T. C., et al. (2011). High-throughput droplet digital PCR system for absolute quantitation of DNA copy number. Anal Chem 83, 8604-8610.

Hodgson, J. G., Agopyan, N., Gutekunst, C. A., Leavitt, B. R., LePiane, F., Singaraja, R., Smith, D. J., Bissada, N., Mccutcheon, K., Nasir, J., et al. (1999). A YAC mouse model for Huntington's disease with full-length mutant huntingtin, cytoplasmic toxicity, and selective striatal neurodegeneration. Neuron 23, 181-192.

Hsu, P. D., Lander, E. S., and Zhang, F. (2014). Development and applications of CRISPR-Cas9 for genome engineering. Cell 157, 1262-1278.

Huntingtons Disease Collaborative (1993). A novel gene containing a trinucleotide repeat that is expanded and unstable on Huntington's disease chromosomes. Cell 72, 971-983.

Keeler, A. M., Sapp, E., Chase, K., Sottosanti, E., Danielson, E., Pfister, E., Stoica, L., DiFiglia, M., Aronin, N., and Sena-Esteves, M. (2016). Cellular Analysis of Silencing the Huntington's Disease Gene Using AAV9 Mediated Delivery of Artificial Micro RNA into the Striatum of Q140/Q140 Mice. J Huntingtons Dis 5, 239-248.

Kordasiewicz, H. B., Stanek, L. M., Wancewicz, E. V., Mazur, C., McAlonis, M. M., Pytel, K. A., Artates, J. W., Weiss, A., Cheng, S. H., Shihabuddin, L. S., et al. (2012). Sustained therapeutic reversal of Huntington's disease by transient repression of huntingtin synthesis. Neuron 74, 1031-1044.

Liu, J. P., and Zeitlin, S. O. (2017). Is Huntingtin Dispensable in the Adult Brain? J Huntingtons Dis 6, 1-17.

Mccullough, K. T., Boye, S. L., Fajardo, D., Calabro, K., Peterson, J. J., Strang, C. E., Chakraborty, D., Gloskowski, S., Haskett, S., Samuelsson, S., et al. (2019). Somatic Gene Editing of GUCY2D by AAV-CRISPR/Cas9 Alters Retinal Structure and Function in Mouse and Macaque. Hum Gene Ther 30, 571-589.

Mckinstry, S. U., Karadeniz, Y. B., Worthington, A. K., Hayrapetyan, V. Y., Ozlu, M. I., Serafin-Molina, K., Risher, W. C., Ustunkaya, T., Dragatsis, I., Zeitlin, S., et al. (2014). Huntingtin is required for normal excitatory synapse development in cortical and striatal circuits. J Neurosci 34, 9455-9472.

Mehler, M. F., Petronglo, J. R., Arteaga-Bracho, E. E., Gulinello, M. E., Winchester, M. L., Pichamoorthy, N., Young, S. K., DeJesus, C. D., Ishtiaq, H., Gokhan, S., et al. (2019). Loss-of-Huntingtin in Medial and Lateral Ganglionic Lineages Differentially Disrupts Regional Interneuron and Projection Neuron Subtypes and Promotes Huntington's Disease-Associated Behavioral, Cellular, and Pathological Hallmarks. J Neurosci 39, 1892-1909.

Merienne, N., Vachey, G., de Longprez, L., Meunier, C., Zimmer, V., Perriard, G., Canales, M., Mathias, A., Herrgott, L., Beltraminelli, T., et al. (2017). The Self-Inactivating KamiCas9 System for the Editing of CNS Disease Genes. Cell Rep 20, 2980-2991.

Miniarikova, J., Zimmer, V., Martier, R., Brouwers, C. C., Pythoud, C., Richetin, K., Rey, M., Lubelski, J., Evers, M. M., van Deventer, S. J., et al. (2017). AAV5-miHTT gene therapy demonstrates suppression of mutant huntingtin aggregation and neuronal dysfunction in a rat model of Huntington's disease. Gene Ther 24, 630-639.

Monteys, A. M., Ebanks, S. A., Keiser, M. S., and Davidson, B. L. (2017). CRISPR/Cas9 Editing of the Mutant Huntingtin Allele In Vitro and In Vivo. Mol Ther 25, 12-23.

Nelson, C. E., Wu, Y., Gemberling, M. P., Oliver, M. L., Waller, M. A., Bohning, J. D., Robinson-Hamm, J. N., Bulaklak, K., Castellanos Rivera, R. M., Collier, J. H., et al. (2019). Long-term evaluation of AAV-CRISPR genome editing for Duchenne muscular dystrophy. Nat Med 25, 427-432.

Palacios, I. M. (2013). Nonsense-mediated mRNA decay: from mechanistic insights to impacts on human health. Briefings in functional genomics 12, 25-36.

Pfister, E. L., DiNardo, N., Mondo, E., Borel, F., Conroy, F., Fraser, C., Gernoux, G., Han, X., Hu, D., Johnson, E., et al. (2018). Artificial miRNAs Reduce Human Mutant Huntingtin Throughout the Striatum in a Transgenic Sheep Model of Huntington's Disease. Hum Gene Ther 29, 663-673.

Pfister, E. L., Kennington, L., Straubhaar, J., Wagh, S., Liu, W., DiFiglia, M., Landwehrmeyer, B., Vonsattel, J. P., Zamore, P. D., and Aronin, N. (2009). Five siRNAs targeting three SNPs may provide therapy for three-quarters of Huntington's disease patients. Current biology: CB 19, 774-778.

Pinello, L., Canver, M. C., Hoban, M. D., Orkin, S. H., Kohn, D. B., Bauer, D. E., and Yuan, G. C. (2016). Analyzing CRISPR genome-editing experiments with CRISPResso. Nat Biotechnol 34, 695-697.

Platt, R. J., Chen, S., Zhou, Y., Yim, M. J., Swiech, L., Kempton, H. R., Dahlman, J. E., Parnas, O., Eisenhaure, T. M., Jovanovic, M., et al. (2014). CRISPR-Cas9 knockin mice for genome editing and cancer modeling. Cell 159, 440-455.

Popp, M. W., and Maquat, L. E. (2013). Organizing principles of mammalian nonsense-mediated mRNA decay. Annual review of genetics 47, 139-165.

Sah, D. W., and Aronin, N. (2011). Oligonucleotide therapeutic approaches for Huntington disease. The Journal of clinical investigation 121, 500-507.

Sena-Esteves, M., Tebbets, J. C., Steffens, S., Crombleholme, T., and Flake, A. W. (2004). Optimized large-scale production of high titer lentivirus vector pseudotypes. J Virol Methods 122, 131-139.

Shin, J. W., Kim, K. H., Chao, M. J., Atwal, R. S., Gillis, T., MacDonald, M. E., Gusella, J. F., and Lee, J. M. (2016). Permanent inactivation of Huntington's disease mutation by personalized allele-specific CRISPR/Cas9. Hum Mol Genet.

Stanek, L. M., Sardi, S. P., Mastis, B., Richards, A. R., Treleaven, C. M., Taksir, T., Misra, K., Cheng, S. H., and Shihabuddin, L. S. (2014). Silencing mutant huntingtin by adeno-associated virus-mediated RNA interference ameliorates disease manifestations in the YAC128 mouse model of Huntington's disease. Hum Gene Ther 25, 461-474.

Walter, D. M., Venancio, O. S., Buza, E. L., Tobias, J. W., Deshpande, C., Gudiel, A. A., Kim-Kiselak, C., Cicchini, M., Yates, T. J., and Feldser, D. M. (2017). Systematic In Vivo Inactivation of Chromatin-Regulating Enzymes Identifies Setd2 as a Potent Tumor Suppressor in Lung Adenocarcinoma. Cancer Res 77, 1719-1729.

Wilson, K. A., Chateau, M. L., and Porteus, M. H. (2013). Design and Development of Artificial Zinc Finger Transcription Factors and Zinc Finger Nucleases to the hTERT Locus. Molecular therapy Nucleic acids 2, e87.

Yang, S., Chang, R., Yang, H., Zhao, T., Hong, Y., Kong, H. E., Sun, X., Qin, Z., Jin, P., Li, S., et al. (2017). CRISPR/Cas9-mediated gene editing ameliorates neurotoxicity in mouse model of Huntington's disease. The Journal of clinical investigation 127, 2719-2724.

Zeitler, B., Froelich, S., Marlen, K., Shivak, D. A., Yu, Q., Li, D., Pearl, J. R., Miller, J. C., Zhang, L., Paschon, D. E., et al. (2019). Allele-selective transcriptional repression of mutant HTT for the treatment of Huntington's disease. Nat Med 25, 1131-1142.

Zeitlin, S., Liu, J. P., Chapman, D. L., Papaioannou, V. E., and Efstratiadis, A. (1995). Increased apoptosis and early embryonic lethality in mice nullizygous for the Huntington's disease gene homologue. Nat Genet 11, 155-163.

Zhu, L. J., Holmes, B. R., Aronin, N., and Brodsky, M. H. (2014). CRISPRseek: a bioconductor package to identify target-specific guide RNAs for CRISPR-Cas9 genome-editing systems. PloS one 9, e108424.

---

We claim:

1. A method, comprising:
   a) providing;
   i) a patient comprising a Huntingtin gene having a heterozygous allele pair, wherein said heterozygous allele pair comprises;
   A) a first allele that expresses a mutant Huntingtin protein, said first allele comprising a target sequence, a single nucleotide polymorphism (SNP) and a protospacer adjacent motif (PAM), wherein said target sequence flanks a mutated gene sequence; and
   B) a second allele without said SNP and expresses a wild type Huntingtin protein;
   ii) a composition comprising a Cas9 nuclease and a single guide ribonucleic acid (sgRNA) molecule, wherein said sgRNA-molecule targets said protospacer adjacent motif;

b) administering said composition to said patient;
c) editing said SNP with single nucleotide specificity with said Cas9 nuclease such that a nonsense codon is created in said first allele; and
d) reducing said mutant Huntingtin protein expression and said wild type Huntingtin protein expression is unaffected.

2. The method of claim 1, wherein said SNP flanks said PAM.

3. The method of claim 1, wherein said SNP resides within said PAM.

4. The method of claim 1, wherein said target sequence is selected from the group consisting of SEQ ID NO: 1-12.

5. The method of claim 1, wherein said sgRNA molecule hybridizes to said PAM.

6. The method of claim 1, wherein said composition further comprises a viral vector, wherein said viral vector encodes said Cas9 nuclease and said sgRNA-molecule.

7. The method of claim 6, wherein said viral vector is a lentivirus vector.

8. The method of claim 6, wherein said viral vector is an adenovirus vector.

9. The method of claim 1, wherein said composition further comprises a plasmid molecule, said plasmid molecule encoding said Cas9 nuclease and said sgRNA molecule.

10. The method of claim 1, wherein said Cas9 nuclease is hybridized to said sgRNA.

11. The method of claim 1, wherein said sgRNA comprises a crRNA and a tracrRNA.

* * * * *